US011868905B1

(12) United States Patent
Christie, IV et al.

(10) Patent No.: US 11,868,905 B1
(45) Date of Patent: *Jan. 9, 2024

(54) CLINICAL DECISION SUPPORT SYSTEMS, APPARATUS, AND METHODS

(71) Applicant: ALLSCRIPTS SOFTWARE, LLC, Chicago, IL (US)

(72) Inventors: Samuel H. Christie, IV, Cary, NC (US); Bryn Rhodes, Orem, UT (US)

(73) Assignee: Allscripts Software, LLC, Chicago, IL (US)

( * ) Notice: Subject to any disclaimer, the term of this patent is extended or adjusted under 35 U.S.C. 154(b) by 897 days.

This patent is subject to a terminal disclaimer.

(21) Appl. No.: 16/590,185

(22) Filed: Oct. 1, 2019

Related U.S. Application Data

(63) Continuation of application No. 13/454,915, filed on Apr. 24, 2012, now Pat. No. 10,452,981.

(60) Provisional application No. 61/502,865, filed on Jun. 30, 2011.

(51) Int. Cl.
  *G06N 5/02* (2023.01)
  *G16H 10/60* (2018.01)
  *G06Q 50/22* (2018.01)

(52) U.S. Cl.
  CPC ............... *G06N 5/02* (2013.01); *G06Q 50/22* (2013.01); *G16H 10/60* (2018.01)

(58) Field of Classification Search
  USPC .......................................................... 706/47
  See application file for complete search history.

(56) References Cited

U.S. PATENT DOCUMENTS

| 5,810,747 | A | 9/1998 | Brudny et al. |
| 6,865,565 | B2 | 3/2005 | Rainsberger et al. |
| 6,868,565 | B2 | 3/2005 | Frey |
| 7,222,113 | B2 | 5/2007 | Katz |
| 7,869,591 | B1 * | 1/2011 | Nagel .................. H04L 63/061 380/282 |
| 8,880,454 | B2 | 11/2014 | Christie, IV et al. |
| 2008/0091465 | A1 * | 4/2008 | Fuschino ............... G06Q 10/06 705/2 |
| 2008/0222132 | A1 | 9/2008 | Pan et al. |

(Continued)

FOREIGN PATENT DOCUMENTS

WO 2010141251 A2 12/2010

*Primary Examiner* — Sakinah White Taylor
(74) *Attorney, Agent, or Firm* — Peter Zura; LOZA & LOZA, LLP

(57) ABSTRACT

A system includes a centralized repository for tracking rule content and managing subscriptions to rule content by organizations and providers utilizing the system; a rule-evaluation server for receiving requests for rule-evaluations for specific patients, wherein the server determines content needing to be evaluated and retrieves the content to be used; a rule engine for performing the evaluations, wherein content, patient data, and rule evaluation parameters are provided to the engine, and the engine returns recommendations triggered by the evaluation, if any; an aggregator for aggregating recommendations from multiple sources, detecting and coordinating related recommendations, and applying configuration settings based on the patient and/or provider in context; and a client component for coordinating communication between an electronic health records system, the server, and the aggregator.

20 Claims, 22 Drawing Sheets

(56) References Cited

U.S. PATENT DOCUMENTS

| | | | |
|---|---|---|---|
| 2009/0036750 A1* | 2/2009 | Weinstein | G16H 40/67 |
| | | | 600/300 |
| 2009/0132586 A1* | 5/2009 | Napora | G16H 40/20 |
| 2009/0216558 A1 | 8/2009 | Reisman et al. | |
| 2009/0216562 A1 | 8/2009 | Faulkner et al. | |
| 2009/0287837 A1 | 11/2009 | Felsher | |
| 2010/0063930 A1* | 3/2010 | Kenedy | G06Q 20/3674 |
| | | | 705/51 |
| 2010/0280847 A1 | 11/2010 | Schaffer | |
| 2011/0288877 A1* | 11/2011 | Ofek | G16H 50/20 |
| | | | 707/661 |
| 2011/0301982 A1 | 12/2011 | Green, Jr. | |
| 2012/0110656 A1 | 5/2012 | Santos et al. | |
| 2013/0006910 A1 | 1/2013 | Christie, IV et al. | |
| 2013/0006911 A1 | 1/2013 | Christie, IV et al. | |
| 2013/0006912 A1 | 1/2013 | Christie, IV et al. | |

* cited by examiner

Addition Expression

```
<ds:BinaryExpression Operator="opAdd">
    <ds:ValueExpression Value="2" />
    <ds:ValueExpression Value="2" />
</ds:BinaryExpression>
```

*FIG. 5*

Rule Definition

```xml
<?xml version="1.0" encoding="utf-8" ?>
<ds:DynamicRule
   xmlns="http://schemas.microsoft.com/winfx/2006/xaml/presentation"
   xmlns:ds="http://schemas.allscripts.com/cds/evaluation"
   xmlns:am="http://schemas.allscripts.com/mom"
   xmlns:sys="clr-namespace:System;assembly=mscorlib"
   Name="EmptyRule"
   Description="Empty Rule"
   SeverityID="MED"
>
        <ds:DynamicRule.NamedExpressions>
            <ds:NamedExpression Name="Expression1">
                <ds:ValueExpression Value="True"/>
            </ds:NamedExpression>
        </ds:DynamicRule.NamedExpressions>
        <ds:DynamicRule.Criteria>
            <ds:ExpressionReference Name="Expression1"/>
        </ds:DynamicRule.Criteria>
        <ds:DynamicRule.Assertion>
            <am:MissingDataAssertion          Description="Empty Recommendation" CodeSet="LOINC" Code="9999"/>
        </ds:DynamicRule.Assertion>
</ds:DynamicRule>
```

FIG. 6

Value Expressions

```
<!-- Scalar Value -->
<ds:ValueExpression Value="5"/>

<!-- List Value -->
<ds:ListExpression>
        <!-- Structured Value -->
        <ds:Code CodingSystem="CPT4" CodeValue="19180"/>
        <ds:Code CodingSystem="CPT4" CodeValue="19200"/>
        <ds:Code CodingSystem="CPT4" CodeValue="19220"/>
        <ds:Code CodingSystem="CPT4" CodeValue="19240"/>
</ds:ListExpression>
```

*FIG. 7*

Operations

```xml
<!-- Binary operation (Addition) -->
<ds:BinaryExpression Operator="opAdd">
        <ds:ValueExpression Value="2" />
        <ds:ValueExpression Value="2" />
</ds:BinaryExpression>

<!-- Patient Age -->
<ds:CalculateAge>
        <ds:PropertyExpression Path="DateOfBirth">
                <ds:RequestExpression Type="Patient" Cardinality="Single" />
        <ds:PropertyExpression>
</ds:CalculateAge>

<!-- Logical operations (And and Not) -->
<ds:LogicalConnective Operator="opAnd">
        <ds:ExpressionReference Name ="Denominator"/>
        <ds:UnaryExpression Operator="opNot">
                <ds:ExpressionReference Name="Numerator"/>
        <ds:UnaryExpression>
</ds:LogicalConnective>
```

FIG. 8

Data Access Expressions

```
<!-- Systolic Blood Pressure Measurements Today -->
<ds:RequestExpression Type="VitalSignObservation">
     <ds:ListExpression>
          <ds:Code CodingSystem="ACCDS" CodeValue="V.SYS" />
     </ds:ListExpression>
     <ds:DateRangeWithin Granularity="Day" NumberOfPeriods="0"/>
</ds:RequestExpression>

<!-- Tobacco use within two years -->
<ds:RequestExpression Type="SocialHistory">
     <ds:UnionExpression>
          <!-- TobaccoUser Value Set (SNOMED-CT codes) -->
          <ds"ValueSetExpression ValueSetID="1001"/>
          <ds:ListExpression>
               <!-- TobaccoUser Social History (Allscripts Common CDS CodeSet) -->
               (ds:Code CodingSystem="ACCDS" CodeValue="HS.TBCU" />
          </ds:ListExpression>
     </ds:UnionExpression>
     <ds:DateRangeWithin Granularity="Year" NumberOfPeriods="2" />
</ds:RequestExpression>
```

*FIG. 9*

Set-Based Operations

```xml
<!-- Patient Has Hypertension Diagnosis -->
<ds:UnaryExpression Operator="opExists">
    <ds:FilterExpression>
        <ds:RequestExpression Type="Problem">
            <ds:ValueSetExpression ValueSetID="1000" />
        </ds:RequestExpression>
        <ds:BinaryExpression Operator="opEqual">
            <ds:PropertyExpression Path="Status" />
            <ds:ValueExpression Value="Active" />
        </ds:BinaryExpression>\
    </ds:FilterExpression>
</ds:UnaryExpression>

<!-- FOBT Codes, combined -->
<ds:UnionExpression>
    <ds:ValueSetExpression ValueSetID="1013" />
    <ds:ListExpression>
        <ds:Code CodingSystem="ACCDS" CodeValue="LAB.FOB"/>
    </ds:ListExpression>
</ds:UnionExpression>
```

FIG. 10

Sorting

```xml
<!-- Date of Last LDL Test -->
<ds:PropertyExpression Path="ResultDateTime">
    <ds:UnaryExpression Operator="opLast">
        <ds:SortExpression OrderBy="ResultDateTime">
            <ds:FilterExpression>
                <ds:RequestExpression Type="Result">
                    <ds:ListExpression>
                        <ds:Code CodingSystem="ACCDS" CodeValue="LAB.LDL"/>
                    </ds:ListExpression>
                </ds:RequestExpression>
                <ds:BinaryExpression Operator="opEqual">
                    <ds:PropertyExpression Path="Status"/>
                    <ds:ValueExpression Value="Complete"/>
                </ds:BinaryExpression>
            </ds:FilterExpression>
        </ds:SortExpression>
    </ds:UnaryExpression>
</ds:PropertyExpression>
```

*FIG. 11*

Parameterization

```xml
<!-- Mammography within ScreeningMonths -->
<ds:RequestExpression Type="Procedure">
    <ds:UnionExpression>
        <ds:ValueExpression ValueSetID="1033" />
        <ds:ListExpression>
            <ds:Code CodingSystem="ACCDS" CodeValue="PRC.MAM" />
        </ds:ListExpression>
    </ds:UnionExpression>
    <ds:DateRangeWithin Granularity="Month">
        <ds:ExpressionReference Name="ScreeningMonths"/>
    </ds:DateRangeWithin>
</ds:RequestExpression>
```

*FIG. 12*

Named Expressions

```
<ds:NamedExpression Name="HasHypertension">
    <ds:UnaryExpression Operator="opExists">
        <ds:FilterExpression>
            <ds:RequestExpression Type="Problem">
                <ds:ValueSetExpression ValueSetID="1000" />
            </ds:RequestExpression>
            <ds:BinaryExpression Operator="opEqual">
                <ds:PropertyExpression Path="Status" />
                <ds:ValueExpression Value="Active" />
            </ds:BinaryExpression>
        </ds:FilterExpression>
    </ds:UnaryExpression>
</ds:NamedExpression>

<ds:LogicalConnective Opertator="opAnd">
    <ds:ExpressionReference Name="HasHypertension" />
    <ds:UnaryExpression Operator="opNot">
        <ds:ExpressionReference Name="HasSystolicBPMeasurement" />
    </ds:UnaryExpression>
</ds:LogicalConnective>
```

FIG. 13

Managing Entity | Client Connect

Quick Links
ACTioN Home

Sign in
Please enter your user id and password below to enter the site.

* User ID
* Password

☐ Save this password on my computer for automatic sign in.
*Note:* *Recommended for use on private machines only.*

Submit

*FIG. 14*

Manage Provider Subscriptions
Show my rules only

| | | Provider | | Organization |
|---|---|---|---|---|
| | | 8899900001 | | 82796 |

| | Rule | Name | Description | Subscribed |
|---|------|------|-------------|:----------:|
| + | 2001 | NQF 0013 | Hypertension: Blood Pressure Measurement | ☑ |
| + | 2002 | NQF 0024A and NQF21 | Weight Assessment and Counseling for Child, and Adult Weight Screening | ☑ |
| + | 2003 | NQF 0024B | Weight Assessment and Counseling for Child: Nutrition Counseling | ☑ |
| + | 2004 | NQF 0024C | Weight Assessment and Counseling for Child: Physical Activity Counseling | ☑ |
| + | 2005 | NQF 0028A | Preventive Care and Screening: Tobacco Use Assessment | ☑ |
| + | 2006 | NQF 0028B-1 | Preventive Care and Screening: Tobacco Cessation Intervention | ☑ |
| + | 2007 | NQF 0041 | Preventive Care and Screening: Influenza Immunization for Patients over 6 | ☑ |
| + | 2008 | NQF 0028B-2 | Preventive Care and Screening: Tobacco Cessation Intervention | ☑ |
| + | 3001 | NQF 0028B-2 | Preventive Care Screening: Mammography | ☑ |

FIG. 15

Manage Provider Subscriptions
Show my rules only

| | | Provider | | Organization |
|---|---|---|---|---|
| | | 8899900001 | | 82796 |

| | Rule | Name | Description | Subscribed |
|---|------|------|-------------|:----------:|
| + | 2001 | NQF 0013 | Hypertension: Blood Pressure Measurement | ☑ |
| + | 2002 | NQF 0024A and NQF21 | Weight Assessment and Counseling for Child, and Adult Weight Screening | ☑ |
| + | 2003 | NQF 0024B | Weight Assessment and Counseling for Child: Nutrition Counseling | ☑ |
| + | 2004 | NQF 0024C | Weight Assessment and Counseling for Child: Physical Activity Counseling | ☑ |
| − | 2005 | NQF 0028A | Preventive Care and Screening: Tobacco Use Assessment | ☑ |

▽ Description Details:

Version: 1  (Subscription will be automatically upgraded to highest version)  Lock to this version
Patients 13 years or older that do not have a record of smoking status recorded in Social History within the last year.

Regulatory: Meaningful Use
Recommendation: Tobacco use assessment recommended every 12 months for patient 13 years or older.

▽ Source Info:

| Activation: | 2010-Jan-01 | |
|---|---|---|
| Evidence: | Meaningful Use Prevention Care and Screening Measure: Tobacco Use Assessme | |
| Authors: | Allscripts | http://www.Allscripts.com/ |
| Sponsorship: | Allscripts | http://www.Allscripts.com/ |

FIG. 16

▽ Description Details:
Version: 1  Automatically upgrade to highest version
Patients 13 years or older that do not have a record of smoking status recorded in Social History within the last year.
Regulatory: Meaningful Use
Recommendation: Tobacco use assessment recommended every 12 months for patient 13 years or older.
▽ Source Info:
Activation:  2010-Jan-01
Evidence:  Meaningful Use Prevention Care and Screening Measure: Tobacco Use Assessme
Authors:  Allscripts  http://www.Allscripts.com/
Sponsorship:  Allscripts  http://www.Allscripts.com/

*FIG. 17*

▽ Description Details:
Version: 1  (Subscription will be automatically upgraded to highest version)  Lock to this version
Patients 13 years or older that do not have a record of smoking status recorded in Social History within the last year.
Regulatory: Meaningful Use
Recommendation: Tobacco use assessment recommended every 12 months for patient 13 years or older.
▽ Source Info:
Activation:  2010-Jan-01
Evidence:  Meaningful Use Prevention Care and Screening Measure: Tobacco Use Assessme
Authors:  Allscripts  http://www.Allscripts.com/
Sponsorship:  Allscripts  http://www.Allscripts.com/

*FIG. 18*

| - | 3001 | NQF 0031 | Preventive Care Screening: Mammography | ☑ |

▷ Description Details:
Regulatory: Meaningful Use
Recommendation: Mammogram recommended every 12 months for female patient 40 years or older.
▽ Rule Parameters: (Provider Overrides)  (Save)
  Screening Months  [11]  (Return to default)
▷ Source Info:

*FIG. 19*

| RecommendationTypeDispositionAudit | |
|---|---|
| PK | ID |
| | ChangeType |
| | ChangedOn |
| | ChangedBy |
| | DispositionID |
| | PatientID |
| | ProviderID |
| | UserID |
| | Since |
| | Until |
| | TypeID |
| | CodeSet |
| | Code |
| | SeverityID |
| | EncounterID |
| | StatusID |
| | ReasonID |
| | ReasonDescription |
| | Comment |

| AppliedRecommendationDispositionAudit | |
|---|---|
| PK | ID |
| | ChangeType |
| | ChangedOn |
| | ChangedBy |
| I1 | AppliedDispositionID |
| FK1,I2 | RecommendationID |
| | AppliedProviderID |
| | AppliedUserID |
| | DispositionTypeID |
| | DispositionID |
| | SourceID |
| | PatientID |
| | ProviderID |
| | UserID |
| | EncounterID |
| | Since |
| | Until |
| | StatusID |
| | ReasonID |
| | ReasonDescription |
| | Comment |

| RecommendationDispositionApplicationAudit | |
|---|---|
| PK | ID |
| | AppliedOn |
| | AppliedBy |
| FK1,I1 | RecommendationID |
| | AppliedProviderID |
| | AppliedUserID |

| DispositionReasonAudit | |
|---|---|
| PK | ID |
| | ChangeType |
| | ChangedOn |
| | ChangedBy |
| | ReasonID |
| | Description |
| | ParentID |
| | StatusID |

| RuleDispositionAudit | |
|---|---|
| PK | ID |
| | ChangeType |
| | ChangedOn |
| | ChangedBy |
| | DispositionID |
| | PatientID |
| | ProviderID |
| | UserID |
| | Since |
| | Until |
| | RuleID |
| | SeverityID |
| | EncounterID |
| | StatusID |
| | ReasonID |
| | ReasonDescription |
| | Comment |

| RecommendationDispositionAudit | |
|---|---|
| PK | ID |
| | ChangeType |
| | ChangedOn |
| | ChangedBy |
| | DispositionID |
| | PatientID |
| | ProviderID |
| | UserID |
| | Since |
| | Until |
| | RecommendationID |
| | EncounterID |
| | StatusID |
| | ReasonID |
| | ReasonDescription |
| | Comment |

| AuditType | |
|---|---|
| PK | ID |
| | Description |

| RecommendationAudit | |
|---|---|
| PK | ID |
| FK1,I1 | AuditTypeID |
| | AuditOn |
| | AuditBy |
| FK2,I2 | RecommendationID |
| | ProviderInContextID |
| | EncounterInContextID |
| | ContextID |
| | ContextDescription |
| | UserID |
| | UserName |
| | StatusID |
| | ReasonID |
| | ReasonDescription |
| | Comment |

| RuleParameterAudit | |
|---|---|
| PK | ID |
| | ChangeType |
| | ChangedOn |
| | ChangedBy |
| | RuleID |
| | RuleVersion |
| | PatientID |
| | ProviderID |
| | Name |
| | Since |
| | Value |

*FIG. 23*

CLINICAL DECISION SUPPORT SYSTEMS, APPARATUS, AND METHODS

CROSS-REFERENCE TO RELATED APPLICATION

The present application is a continuation of, and claims priority under 35 U.S.C. § 120 to U.S. patent application Ser. No. 13/454,915 filed Apr. 24, 2012, now U.S. Pat. No. 10,452,981 issued Oct. 22, 2019, which claims priority to U.S. Provisional Application Ser. No. 61/502,865 filed Jun. 30, 2011, each of which is incorporated herein by reference in its entirety.

Additionally, the present application hereby incorporates herein by reference the entire disclosure of the Appendix attached hereto, which includes additional disclosure of aspects and features in accordance with one or more embodiments of the present invention.

COPYRIGHT STATEMENT

All of the material in this patent document, including the computer program listing, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved. The right of reproduction does not extend to any reproduction that occurs in connection with execution of the disclosed software on a computer. No copyright rights are granted for executing the software on a computer, and such rights are explicitly reserved.

COMPUTER PROGRAM LISTING

Submitted concurrently herewith via the USPTO's electronic filing system, and incorporated herein by reference, are computer program files including instructions, routines, and/or other contents of several computer program. A table setting forth the name and size of files included in the computer program listing is included below.

| File Name | Creation Date | File Size (bytes) |
|---|---|---|
| TXT9-ZIP.TXT | 6/29/2011 19:56 | 26153224 |
| CDS15-ZI.TXT | 6/29/2011 19:55 | 24774306 |
| TXT8-ZIP.TXT | 6/29/2011 19:55 | 24682779 |
| EXT4-ZIP.TXT | 6/29/2011 19:55 | 24176177 |
| CDS16-ZI.TXT | 6/29/2011 19:55 | 23560907 |
| TXT10-ZI.TXT | 6/29/2011 19:56 | 23487900 |
| BUS1-ZIP.TXT | 6/29/2011 19:42 | 22633066 |
| CDS107-Z.TXT | 6/29/2011 19:55 | 22516407 |
| TXT2-ZIP.TXT | 6/29/2011 19:55 | 22436780 |
| COMPON1-.TXT | 6/29/2011 19:55 | 21277806 |
| CDS15A-Z.TXT | 6/29/2011 19:55 | 20804633 |
| TXT7-ZIP.TXT | 6/29/2011 19:56 | 20709945 |
| CDS14-ZI.TXT | 6/29/2011 19:55 | 20281259 |
| TXT6-ZIP.TXT | 6/29/2011 19:56 | 20197165 |
| EXT3-ZIP.TXT | 6/29/2011 19:55 | 19761171 |
| BUS2-ZIP.TXT | 6/29/2011 19:42 | 18736216 |
| EXT1-ZIP.TXT | 6/29/2011 19:55 | 18359499 |
| DOC1-ZIP.TXT | 6/29/2011 19:56 | 18332452 |
| DOC2-ZIP.TXT | 6/29/2011 19:55 | 18232060 |
| CDS14A-Z.TXT | 6/29/2011 19:55 | 18083397 |
| TXT5-ZIP.TXT | 6/29/2011 19:56 | 18007028 |
| CDS16A1-.TXT | 6/29/2011 20:14 | 17904496 |
| SPEC1-ZI.TXT | 6/29/2011 19:55 | 17638841 |
| TEST1-ZI.TXT | 6/29/2011 19:55 | 16744536 |
| COMPON2-.TXT | 6/29/2011 19:55 | 15975142 |
| TXT3-ZIP.TXT | 6/29/2011 19:56 | 15323562 |
| CDS13-ZI.TXT | 6/29/2011 19:55 | 14528693 |
| TXT4-ZIP.TXT | 6/29/2011 19:55 | 14467221 |
| TXT1-ZIP.TXT | 6/29/2011 19:55 | 14278245 |
| EXT2-ZIP.TXT | 6/29/2011 19:56 | 13274954 |
| SPEC2-ZI.TXT | 6/29/2011 19:56 | 11843300 |
| TRUNK1-Z.TXT | 6/29/2011 19:56 | 11420529 |
| TEST2-ZI.TXT | 6/29/2011 19:56 | 9367605 |
| CDS16A2-.TXT | 6/29/2011 20:14 | 8595723 |
| CDS12-ZI.TXT | 6/29/2011 19:55 | 7818641 |
| CDS11-ZI.TXT | 6/29/2011 19:55 | 7547960 |
| BUS3-ZIP.TXT | 6/29/2011 19:42 | 6431109 |
| RULEAU15.TXT | 6/29/2011 19:56 | 4424974 |
| CDS10-ZI.TXT | 6/29/2011 19:55 | 3753950 |
| RULEAU-Z.TXT | 6/29/2011 19:55 | 3567371 |
| TESTH12A.TXT | 6/29/2011 19:55 | 2413897 |
| REL1-ZIP.TXT | 6/29/2011 19:55 | 988106 |
| CDS107U2.TXT | 6/29/2011 19:50 | 82758 |
| CDS131U-.TXT | 6/29/2011 19:55 | 45639 |
| CREF_XSD.TXT | 6/29/2011 19:55 | 21698 |
| SVN1-ZIP.TXT | 6/29/2011 19:55 | 6230 |
| readme.txt | 06/30/2011 00:59 | 2,121,905 |

One of these files, "readme.txt", contains instructions for extracting information from other of the files. These other files are compressed binary files that have been converted to ascii format. These files can be converted back to a compressed .zip archive utilizing an assembly conversion program, source code for which is contained in "readme.txt". The readme file includes instructions for compiling and running this conversion program, and instructions for converting the other text files to compressed, binary files, as well as instructions for recreating a directory structure for these compressed files.

Some of these compressed, binary files include source code written in C Sharp that can be compiled utilizing Microsoft Visual Studio 2008. The target environment for implementations utilizing such source code is 32-bit or 64-bit Windows XP, Vista, or 7.

Additionally, some of these compressed, binary files include compiled HTML help files which include disclosure of aspects and features in accordance with one or more embodiments of the present invention.

BACKGROUND OF THE INVENTION

The present invention generally relates to the expression and evaluation of clinical decision support logic.

In designing a clinical decision support system, it can be useful to provide the ability to evaluate patient information for triggers that will result in recommendations being returned to the provider at the point-of-care. Although several HL7 standard syntaxes exist for the expression of clinical decision support logic, a need exists for improvement in such expression and evaluation of clinical decision support logic. This, and other needs, are addressed by one or more aspects of the present invention.

SUMMARY OF THE INVENTION

The present invention includes many aspects and features. Moreover, while many aspects and features relate to, and are described in, the context of the expression and evaluation of clinical decision support logic, the present invention is not limited to use only in this context, as will become apparent from the following summaries and detailed descriptions of aspects, features, and one or more embodiments of the present invention.

A first aspect of the present invention relates to a clinical decision support system comprising a platform for the expression and delivery of clinical decision support logic on a subscription basis.

Another aspect of the present invention relates to a clinical decision support system comprising a mechanism to ensure that rule evaluation requests can be processed in a timely manner by reducing the overall message size for each request, resulting in diminished overall bandwidth requirements for a rule-processing server.

In a feature of this aspect, the mechanism is built into the content definition and the call-level interface, whereby the request size can be tuned dynamically. In one or more implementations, the only information that is sent is that which will actually be used by rule logic to which a provider is subscribed, whereby the overall size of rule evaluation requests being sent by each provider is reduced when compared to requests that include additional information.

Another aspect of the present invention relates to software comprises computer-executable instructions in computer-readable medium for performing a method as disclosed herein.

Another aspect of the present invention relates to a clinical decision support system ("CDS System") which includes: a centralized repository for tracking rule content and managing subscriptions to rule content by organizations and providers utilizing the CDS System; a CDS Server comprising a rule-evaluation server, wherein clients utilizing the CDS System communicate with the CDS Server to request rule-evaluation for specific patients, and wherein the CDS Server communicates with the CDS Manager to determine which content needs to be evaluated and to retrieve the actual content to be used; a CDS Common Rule Engine comprising an engine responsible for performing the evaluation, wherein the content, patient data, and rule evaluation parameters are provided to the engine, and the engine returns recommendations triggered by the evaluation, if any; a Recommendation Aggregator comprising a component responsible for aggregating recommendations from multiple sources, for detecting and coordinating duplicates, and for applying configuration settings based on the patient and/or provider in context; and a CDS Client comprising a client component responsible for coordinating communication between the consuming EHR, the CDS Server, and the Recommendation Aggregator.

In a feature of one or more aspects, coordinating duplicates includes eliminating duplicates.

In a feature of one or more aspects, the rule-evaluation server is stateless.

In a feature of one or more aspects, the rule-evaluation server is not stateless. In at least some implementations, state information is maintained at the server. In at least some implementations, this state information is not available to a client system.

In a feature of this aspect the system makes available, as part of a call-level interface exposed by the CDS Server and utilized by the CDS Client, a description of the patient data that must be provided in order to successfully perform an evaluation. In at least some implementations, the information is cached so that the call only needs to be made once per EHR per provider for some period, and allows the actual evaluation request to be seeded with only that information that will actually be referenced by the rules to which the calling provider is actually subscribed.

In a feature of this aspect, the system comprises a platform for the expression and delivery of clinical decision support logic on a subscription basis.

In a feature of this aspect, the only information that is sent is that which will actually be used by the rule logic to which a provider is subscribed, whereby the overall size of rule evaluation requests being sent by each provider is reduced when compared to requests that include additional information.

In a feature of this aspect, rule content contains parameters for specific values, rather than being hard-coded as part of the rule content, whereby a provider is able to control whether a recommendation is triggered for a specific patient or practice. In at least some implementations, the parameterization provides a mechanism to ensure that medical providers can tailor the results of the clinical decision support process to the needs of their specific practice and patients without needing to modify rule content.

In a feature of this aspect, the format used to encode clinical decision support logic specifies logic at the functional level such that any need for language syntax is obviated.

In a feature of this aspect, clinical decision support is provided in real-time.

In a feature of this aspect, the size of the evaluation request is dynamically controlled by defining the patient information that must be sent in the request.

In a feature of this aspect, rule evaluation logic is customized through the use of provider-specific parameterization.

In a feature of this aspect, rule evaluation logic is customized through the use of parameterization of the rule logic without redefining the rule itself. In some implementations, such parameterization may be specific to a patient, provider, provider group, and/or practice.

In a feature of this aspect, human readable content is generated using token replacement of values evaluated using the engine.

Another aspect of the present invention relates to a system which includes: a centralized repository for tracking rule content and managing subscriptions to rule content by organizations and providers utilizing the system; a rule-evaluation server for receiving requests for rule-evaluations for specific patients, wherein the server determines content needing to be evaluated and retrieves the content to be used; a rule engine for performing the evaluations, wherein content, patient data, and rule evaluation parameters are provided to the engine, and the engine returns recommendations triggered by the evaluation, if any; an aggregator for aggregating recommendations from multiple sources, detecting and coordinating duplicates, and applying configuration settings based on the patient and/or provider in context; and a client component for coordinating communication between an electronic health records system, the server, and the aggregator.

Another aspect of the present invention relates to a method for facilitating the real-time provision of recommendations to a health care provider. The method includes electronically receiving, from an electronic health records application, a call to evaluate rules associated with healthcare provision; determining, using one or more computer processors, a list of rules subscribed to by a healthcare provider, electronically communicating rules from the list of rules to a rule agent loaded on one or more computing devices; automatically determining specific healthcare information necessary to evaluate rules in the list of rules; electronically communicating the specific healthcare information to the rule agent; evaluating, at the rule agent, the communicated rules of the list of rules utilizing the communicated specific healthcare information; communicating, by the rule agent, one or more results based on the evaluation of the rules, the one or more results comprising one or more recommendations; and receiving, at the electronic health records application, the one or more recommendations.

In a feature of this aspect, the method further includes displaying, to a user at an electronic display via the electronic health records application, text corresponding to at least one of the one or more recommendations.

In a feature of this aspect, the one or more recommendations include human readable recommendation content.

In a feature of this aspect, the one or more recommendations include EHR actionable recommendation content.

In a feature of this aspect, the step of determining, using one or more computer processors, a list of rules subscribed to by a healthcare provider is performed at a manager component configured to obviate the need to access health records.

In a feature of this aspect, the method further includes a step of receiving, via the electronic health records application, a disposition to apply to a displayed recommendation.

In a feature of this aspect, at least one of the rules of the list of rules includes a parameter.

In a feature of this aspect, the method further includes a step of modifying, by a healthcare provider, one or more subscriptions to one or more rules via an interface of a console. In at least some implementations, the step of modifying one or more subscriptions comprises subscribing to a rule. In at least some implementations, the step of modifying one or more subscriptions comprises unsubscribing to a rule. In at least some implementations, the step of modifying one or more subscriptions comprises subscribing to a particular version of a rule. In at least some implementations, the step of modifying one or more subscriptions comprises indicating a desire for a subscription to automatically be updated to the most current version of a rule.

In a feature of this aspect, the one or more results include one or more suggestions. In at least some implementations, each of the one or more suggestions is associated with a recommendation. In at least some implementations, the one or more suggestions include a missing data suggestion. In at least some implementations, the one or more suggestions include an out-of-range suggestion.

In a feature of this aspect, the step of determining, using one or more computer processors, a list of rules subscribed to by a healthcare provider, comprises accessing a cached list of rules subscribed to by a healthcare provider. In at least some implementations, the method further includes a step of receiving update information regarding a list of rules subscribed to by a healthcare provider, and updating the cached list of rules. In at least some implementations, refetching is utilized to compensate for cache aging. In at least some implementations, the aging mechanism is based on the expiration date of the provider subscription. When a subscription entry expires, the cache is updated with the latest entry for that subscription for that provider.

In a feature of this aspect, the step of evaluating, at the rule agent, the communicated rules of the list of rules utilizing the communicated specific healthcare information comprises evaluating the communicated rules using a stateless engine. In at least some implementations, an engine configured to handle null values is utilized.

In a feature of this aspect, the step of evaluating, at the rule agent, the communicated rules of the list of rules utilizing the communicated specific healthcare information comprises evaluating the communicated rules using an engine configured to accommodate multiple states.

Another aspect of the present invention relates to a method for facilitating the real-time provision of recommendations to a health care provider. The method includes steps of electronically receiving a call to evaluate rules associated with healthcare provision; determining, using one or more computer processors, a list of rules subscribed to by a healthcare provider; electronically communicating rules of the list of rules to a rule agent loaded on one or more computing devices; automatically determining specific healthcare information necessary to evaluate rules in the list of rules; electronically communicating the specific healthcare information to the rule agent; evaluating, at the rule agent, the communicated rules of the list of rules utilizing the communicated specific healthcare information; and communicating, by the rule agent, one or more results based on the evaluation of the rules, the one or more results comprising one or more recommendations.

Another aspect of the present invention relates to a method for facilitating the real-time provision of recommendations to a health care provider. The method includes electronically receiving, at a server component loaded on one or more electronic devices from an electronic health records application, a call to evaluate rules associated with healthcare provision; determining, at a manager component loaded on one or more electronic devices, a list of rules subscribed to by a healthcare provider; electronically communicating, by the manager component, the list of rules to the server component; grouping, by the server component, rules of the list of rules into one or more groups based on a respective rule agent necessary to evaluate the rules; communicating, by the server component, a first group of rules to be evaluated to a first rule agent; receiving, at the first rule agent, the first group of rules; automatically determining specific healthcare information necessary to evaluate the rules in the first group; receiving, at the first rule agent, the specific healthcare information necessary to evaluate the rules in the first group; evaluating, at the first rule agent, the rules in the first group of rules utilizing the received specific healthcare information; communicating, by the first rule agent to the server component, one or more results based on the evaluation of the rules in the first group, the one or more results comprising one or more recommendations; and receiving, at the electronic health records application, the one or more recommendations and displaying, to a user at an electronic display via the electronic health records application, text corresponding to one of the one or more recommendations.

In a feature of this aspect, the method further comprises the step of communicating, by the server component, a second group of rules to a second rule agent.

Another aspect of the present invention relates to a method for facilitating the real-time provision of recommendations to a health care provider. The method includes steps of receiving, from an electronic health records application, a user's identity; automatically determining a list of rules subscribed to by a healthcare provider, automatically determining specific information necessary to evaluate the rules from the list of rules, all of the determined specific information being necessary to evaluate one or more of the rules such that the determined specific information is the minimum possible set of information necessary to evaluate the subscribed rules; constructing a message containing only the minimum required information in a request for rule evaluation; and communicating the constructed message for rule evaluation.

In a feature of this aspect, the step of automatically determining a list of rules subscribed to by a healthcare provider comprises automatically determining, using one or more processors, a list of rules subscribed to by a healthcare provider.

In a feature of this aspect, the step of communicating the constructed message for rule evaluation comprises communicating the constructed message to a rule evaluation engine for rule evaluation.

Another aspect of the present invention relates to a system which comprises: one or more electronic devices, each electronic device comprising one or more processors; and one or more computer readable media containing computer executable instructions. The computer executable instructions of the one or more electronic devices are configured to collectively perform a method comprising the steps: of electronically receiving, from an electronic health records application, a call to evaluate rules associated with healthcare provision; determining a list of rules subscribed to by a healthcare provider; electronically communicating rules of the list of rules to a rule agent loaded on one or more computing devices; automatically determining specific healthcare information necessary to evaluate rules in the list of rules; electronically communicating the specific healthcare information to the rule agent; evaluating, at the rule agent, the communicated rules of the list of rules utilizing the communicated specific healthcare information; communicating, by the first rule agent, one or more results based on the evaluation of the rules in the first group, the one or more results comprising one or more recommendations; and receiving, at the electronic health records application, the one or more recommendations and displaying, to a user at an electronic display via the electronic health records application, text or action options corresponding to at least one of the one or more recommendations.

Another aspect of the present invention relates to a clinical decision support system (CDS System). The system includes a CDS manager, loaded on one or more electronic devices, comprising a centralized repository for tracking rule content and managing subscriptions to rule content by organizations and providers utilizing the CDS system; a CDS server, loaded on one or more electronic devices, comprising a rule-evaluation server, wherein clients utilizing the CDS system communicate with the CDS server to request rule-evaluation for specific patients, and wherein the CDS server communicates with the CDS manager to determine which content needs to be evaluated and to retrieve the actual content to be used; a CDS rule engine, loaded on one or more electronic devices, comprising an engine responsible for performing the evaluation, wherein the content, patient data, and rule evaluation parameters are provided to the engine, and the engine returns recommendations triggered by the evaluation, if any; a recommendation aggregator, loaded on one or more electronic devices, comprising a component responsible for aggregating recommendations from multiple sources, detecting and eliminating duplicates, and applying configuration settings based on the patient and/or provider in context; and a CDS client, loaded on one or more electronic devices, comprising a client component responsible for coordinating communication between the consuming rule engine, the CDS server, and the recommendation aggregator. At least some rule content is parameterized in that rule content corresponding to one or more specific rules contains parameters associated with default or user-specified values, rather than values hard-coded as part of the rule content, and the system provides a user interface which allows a provider to customize such parameters by specifying a particular value for a particular parameter.

In a feature of this aspect, the parameterized rule content includes parameters that allow a user to customize a value that determines whether a recommendation is triggered.

In at least some implementations, the system is configured to allow a user to customize a value, for a specific patient, that determines whether a recommendation is triggered for that specific patient, without altering rule content for other patients.

In at least some implementations, the system is configured to allow a provider to customize a value that determines whether a recommendation is triggered for his or her entire practice.

In a feature of this aspect, the parameterized rule content includes parameters that allow a user to customize recommendation output.

In at least some implementations, the system is configured to allow a user to customize a value, for a specific patient, that customizes recommendation output for that specific patient, without altering rule content for other patients.

In at least some implementations, the system is configured to allow a user to customize a value that customizes recommendation output for his or her entire practice.

In a feature of this aspect, the parameterized rule content includes parameters that allow a user to customize recommendation output for a specific patient or practice.

In a feature of this aspect, as part of a call-level interface exposed by the CDS server and utilized by the CDS client, the system makes available a description of the patient data that must be provided in order to successfully perform an evaluation.

In at least some implementations, the information is cached so that the call only needs to be made once per EHR per provider.

In a feature of this aspect, the system comprises a platform for the expression and delivery of clinical decision support logic on a subscription basis.

In a feature of this aspect, the only information that is sent is that which will actually be used by the content to which a provider is subscribed.

In a feature of this aspect, the format used to encode clinical decision support logic specifies logic at the functional level such that any need for language syntax is obviated.

In a feature of this aspect, wherein clinical decision support is provided in real-time to a provider with a patient in a point-of-care setting.

Another aspect of the present invention relates to a method for facilitating the real-time provision of recommendations to a health care provider. The method includes electronically receiving a call to evaluate rules associated with healthcare provision; determining, using one or more computer processors, rule content subscribed to by a healthcare provider, the rule content including one or more parameters representing a user-editable value; electronically communicating rule content to a rule agent loaded on one or more computing devices; automatically determining specific healthcare information necessary to evaluate rules of the rule content; electronically communicating the specific healthcare information to the rule agent; evaluating, at the rule agent, the communicated rules of the rule content utilizing the communicated specific healthcare information, the evaluation taking into account values of the one or more parameters of the rule content; and communicating, by the rule agent, one or more results based on the evaluation of the rules, the one or more results comprising one or more recommendations.

In a feature of this aspect, the method further includes a step of electronically updating a parameter value in response to receiving input from a user input via an electronic device.

In at least some implementations, the updated value is associated with a specific patient.

Another aspect of the present invention relates to a method for facilitating the real-time provision of recommendations to a health care provider. The method includes electronically receiving a call to evaluate rules associated with healthcare provision; determining, using one or more computer processors, rule content subscribed to by a healthcare provider, the rule content including one or more parameters representing a user-editable value; electronically communicating rule content to a rule agent loaded on one or more computing devices; automatically determining specific healthcare information necessary to evaluate rules of the rule content; electronically communicating the specific healthcare information to the rule agent; evaluating, at the rule agent, the communicated rules of the rule content utilizing the communicated specific healthcare information; and communicating, by the rule agent, one or more results based on the evaluation of the rules, the one or more results comprising one or more recommendations. At least one of the one or more recommendations represents a customized recommendation that has been customized based on a value of the one or more or parameters of the rule content.

In a feature of this aspect, the method further includes a step of electronically updating a parameter value in response to receiving input from a user input via an electronic device.

In a feature of this aspect, the updated value is associated with a specific patient.

Another aspect of the present invention relates to a method for coordinating healthcare recommendations. The method includes receiving a plurality of automatically generated healthcare recommendations, each healthcare recommendation including a source therefor, determining one or more sets of two or more recommendations of the plurality of recommendations that are related; combining each set of related recommendations into a single combined recommendation listing multiple sources; and communicating a coordinated list of recommendations, the coordinated list of recommendations including each combined recommendation.

In a feature of this aspect, the method further includes a step of presenting recommendations of the coordinated list of recommendations to a user, the presented recommendations including each combined recommendation.

In at least some implementations, the step of presenting recommendations of the coordinated list of recommendations to a user comprises presenting source information for the combined recommendation to the user.

In at least some implementations, the step of presenting recommendations to a user comprises presenting recommendations to a user via an electronic display.

In a feature of this aspect, one of the sets of related recommendations comprises two or more duplicate recommendations.

In a feature of this aspect, the determining step comprises an automatic determination using one or more processors.

In a feature of this aspect, the automatically generated healthcare recommendations were automatically generated based on rules by a rule evaluation engine.

Another aspect of the present invention relates to a method for coordinating healthcare recommendations. The method includes receiving a plurality of automatically generated healthcare recommendations, each received healthcare recommendation including a source therefor; comparing the received plurality of healthcare recommendations to stored healthcare recommendations, and determining that one or more particular healthcare recommendations of the received plurality of healthcare recommendations is related to one or more particular healthcare recommendations of the stored healthcare recommendations; combining the one or more particular healthcare recommendations of the received plurality of healthcare recommendations with the one or more particular healthcare recommendations of the stored healthcare recommendations into a single combined recommendation listing multiple sources; and communicating a coordinated list of recommendations, the coordinated list of recommendations including the combined recommendation.

In a feature of this aspect, the method further includes a step of presenting recommendations of the coordinated list of recommendations to a user, the presented recommendations including each combined recommendation.

In at least some implementations, the step of presenting recommendations of the coordinated list of recommendations to a user comprises presenting source information for the combined recommendation to the user.

In at least some implementations, the step of presenting recommendations to a user comprises presenting recommendations to a user via an electronic display.

In a feature of this aspect, determining that one or more particular healthcare recommendations of the received plurality of healthcare recommendations is related to one or more particular healthcare recommendations of the stored healthcare recommendations comprises determining that one particular healthcare recommendation of the received plurality of healthcare recommendations is identical to one particular healthcare recommendation of the stored healthcare recommendations.

In a feature of this aspect, the recited determination comprises an automatic determination using one or more processors.

In a feature of this aspect, the automatically generated healthcare recommendations were automatically generated based on rules by a rule evaluation engine.

Another aspect of the present invention relates to a method for coordinating healthcare recommendations. The method includes receiving a plurality of automatically generated healthcare recommendations, each received healthcare recommendation including a source therefor; comparing the received plurality of healthcare recommendations to stored healthcare recommendations, and determining that one or more particular healthcare recommendations of the received plurality of healthcare recommendations is related to one or more particular healthcare recommendations of the stored healthcare recommendations; determining, based on information related to the one or more particular healthcare recommendations of the stored healthcare recommendations, that the one or more particular healthcare recommendations of the received plurality of healthcare recommendations should be suppressed during subsequent presentation of recommendations to a user; communicating a coordinated list of recommendations based on the received plurality of healthcare recommendations; presenting recommendations of the communicated coordinated list of recommendations to a user, the presented recommendations not including the one or more particular healthcare recommendations of the received plurality of healthcare recommendations based on the determination that the one or more particular healthcare recommendations of the received plurality of healthcare recommendations should be suppressed.

In a feature of this aspect, the step of presenting recommendations to a user comprises presenting recommendations to a user via an electronic display.

In a feature of this aspect, the determination based on information related to the one or more particular healthcare recommendations of the stored healthcare recommendations is based on one or more dispositions of the one or more particular healthcare recommendations of the stored healthcare recommendations.

In at least some implementations, one of the one or more dispositions of the one or more particular healthcare recommendations of the stored healthcare recommendations is applied to the one or more particular healthcare recommendations of the received plurality of healthcare recommendations.

In a feature of this aspect, the recited determination comprises an automatic determination using one or more processors.

In a feature of this aspect, the automatically generated healthcare recommendations were automatically generated based on rules by a rule evaluation engine.

Additional aspects and features are disclosed in the Appendix hereof, which is incorporated herein by reference.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings briefly described below, wherein the same elements are referred to with the same reference numerals.

FIG. 5 illustrates an expression for adding the integer values 2 and 2 in accordance with one or more preferred embodiments of the present invention.

FIG. 6 illustrates a simple rule definition in accordance with one or more preferred embodiments of the present invention.

FIG. 7 illustrates exemplary fragments for value expressions for a scalar value and a list value in accordance with one or more preferred embodiments of the present invention.

FIGS. 8-13 include exemplary language fragments illustrating various functionality in accordance with one or more preferred embodiments of the present invention.

FIG. 14 illustrates a login interface of a CDS console of a clinical decision support system in accordance with one or more preferred embodiments of the present invention.

FIGS. 15-19 illustrate a Manage Provider Subscriptions interface of a CDS console in accordance with one or more preferred embodiments of the present invention.

FIG. 23 is a block diagram of a data model for the aggregator audit structures of a clinical decision support system in accordance with one or more preferred embodiments of the present invention.

DETAILED DESCRIPTION

Figure 1:
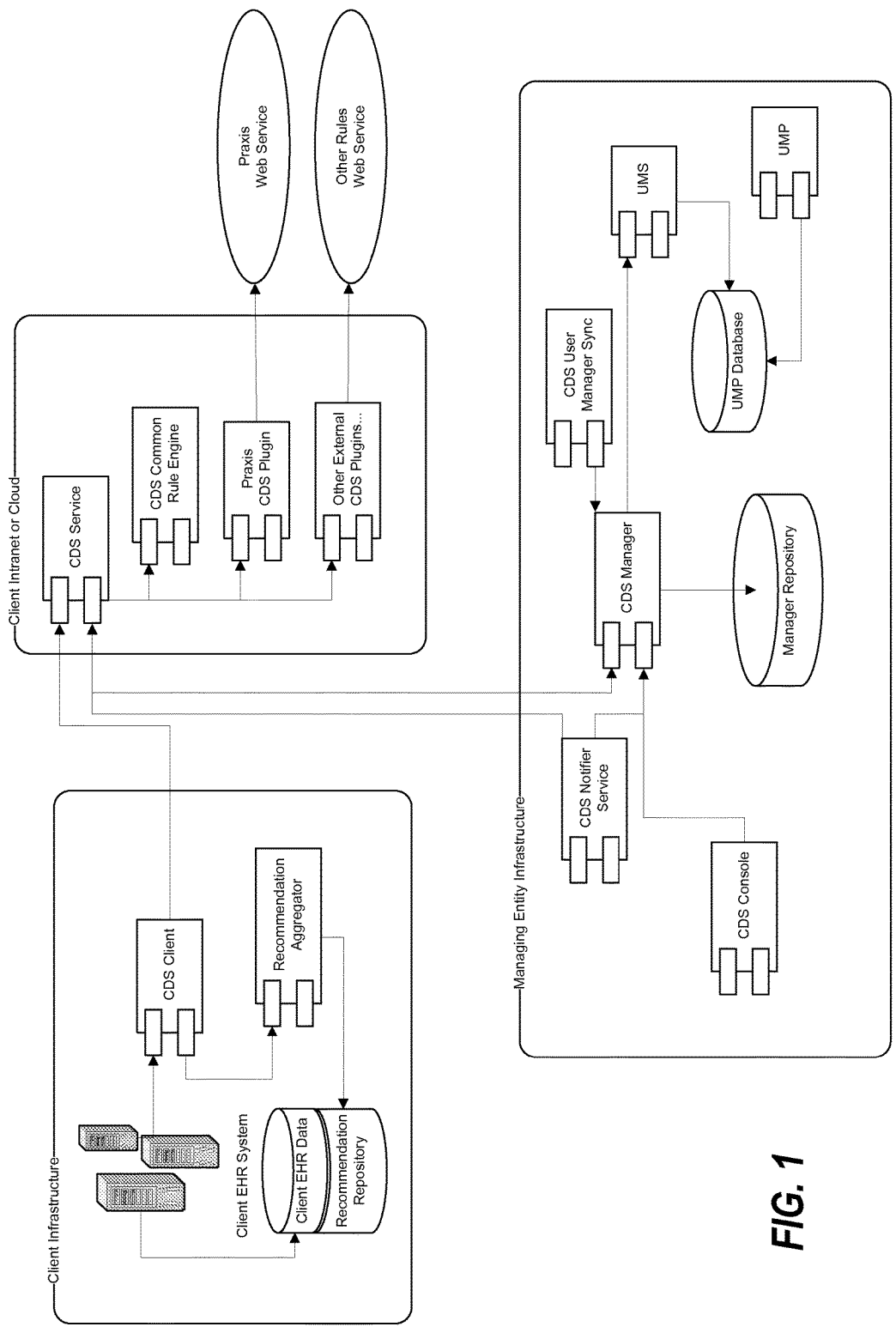
FIGS. 1-4 are block diagrams illustrating a high-level architecture of a clinical decision support system in accordance with one or more preferred embodiments of the present invention.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112. ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein. "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items. "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

CDS Systems in accordance with one or more preferred embodiments of the present invention are described herein. Preferably, such a CDS System provides the ability to evaluate patient information for triggers that will result in recommendations being returned to a healthcare provider in a point-of-care context, e.g., while with a patient. In preferred implementations, such evaluation is performed via the use of rules, which are utilized to generate recommendations and suggestions for patients.

A recommendation is an evidence-based guideline associated with one or more suggestions to be made whenever a particular set of criteria is met for a given patient. For example, consider an exemplary rule that a patient diagnosed with Diabetes Mellitus should have a Hemoglobin A1c level under a certain threshold. If a particular patient matches the diagnosis and has an A1c level exceeding that threshold, a recommendation is returned describing the reason for the recommendation, and potentially providing one or more associated suggestions to help provide improved quality of care.

A suggestion represents specific information that may be provided to a provider, or a step that a provider may be able to take, in order to improve quality of care for a patient identified by a particular rule. In at least some implementations, suggestions can be characterized as belonging to one of several varieties. For example, in preferred implementations, suggestions include out-of-range suggestions and missing data suggestions.

An out-of-range suggestion indicates that a particular data point is outside a range defined as acceptable by the rule producing the suggestion. For example, if a particular rule states that Hemoglobin A1c levels for patients diagnosed with Diabetes Mellitus should be at or below 9.0, the recommendation returned for a patient matching the rule criteria would include an out-of-range suggestion informing a provider that the patient's Hemoglobin A1c level is above the threshold. Preferably, such a suggestion specifies the threshold, as well as the patient's Hemoglobin A1c level.

A missing data suggestion indicates that a particular piece of information is missing. For example, if a particular rule states that female patients between the ages of 40 and 69 should receive a mammogram at least once every 24 months, the recommendation returned for a patient matching the rule criteria would include a missing data suggestion specifying that the patient should be scheduled for a mammogram. Preferably, this is only the case if there is no record of a scheduled appointment. If an appointment record exists but is older than the specified range, then the result would be an out-of-range recommendation. On the other hand, a missing data suggestion might fire if a patient's age or date of birth are not supplied.

A disposition indicates the status of a particular recommendation or type of recommendation. For example, if a particular patient has declined to follow a given suggestion for whatever reason, the provider may indicate that that recommendation should no longer be displayed for the patient.

Dispositions can be applied in three different ways: to a specific recommendation; to all recommendations with a specific code (e.g. LOINC:4548-5); to all recommendations from a specific rule (e.g. NQF #13).

In addition, a disposition can be associated with one or more disposition levels, which determine when a disposition should apply. In a preferred implementations, a disposition can be associated with the following levels (in order of precedence): "patient, provider, and user"; "provider and user"; "patient and user"; "user"; "patient and provider"; "provider"; and "patient". For example, a disposition configured at the patient and provider level is preferably used before a disposition configured at the patient level.

Dispositions preferably can further be associated with disposition reasons. Disposition reasons allow users to provide a reason for a status change. In some preferred implementations, a CDS Aggregator includes a default list of system-defined reasons. Preferably, system-defined reasons cannot be modified, but new reasons can be added if necessary. In some preferred implementations, when a new reason is added, it is added as a sub-reason of one of the system-defined reasons. For reporting purposes, all sub-reasons are preferably more specific types of reasons related to the main reason. In at least some implementations, however, reasons, including system-defined reasons, can be edited, and new reasons or sub-reasons defined, for any reason at all.

Preferably, dispositions further support options relating to: comments, which represent a free text note describing more details about the status change; expiration, supported by a date field indicating when the disposition should no longer apply; and an option to apply to encounter, which can be implemented via a check box indicating whether the disposition should only apply to the current encounter.

In one or more preferred implementations, a CDS System is organized into several major components, each serving a different role in enabling overall functionality of the system. Exemplary such components will now be described in more detail.

CDS Manager

A first of these components is a CDS manager. The CDS Manager is a centralized repository that manages rule definitions and rule subscriptions (described hereinbelow) for providers and organizations using proprietary software (source code for exemplary such proprietary software is provided herewith as a computer program listing). As described in more detail hereinbelow, an "organization" represents the levels of the organizational hierarchy of an organization using a CDS System; a "provider" represents a medical care practitioner that can use a software application that communicates with the CDS System to provide real-time care recommendations; and a "subscription" includes the set of rules that will be evaluated for a given provider and organization.

The CDS Manager maintains a model of an organizational hierarchy in place at each installation (which represents a software site that will use the CDS System and is described in more detail hereinbelow) for the purposes of describing available rules and default subscriptions, as well as allowing providers and directors to manage their specific subscriptions.

Preferably, the CDS Manager does not manage or utilize any patient-specific information.

The CDS Manager uses provider subscription and rule content information to determine which rules need to be evaluated for a given provider and organization. This information is made available through a service interface so that one or more other components of the system, such as, for example, the CDS Server, can determine which rules need to be evaluated without having to be aware of any of the subscription information or structure of the organization.

CDS Console

The CDS System preferably further includes a CDS Console, which in at least some implementations is implemented as a web site that provides one or more user-interfaces to manage the information contained in the CDS Manager. Preferably, there are four main areas of functionality provided by the Console: (1) Administration; (2) Publishing; (3) Organization Subscription Management; and (4) Provider Subscription Management.

The Administration section of the Console allows administrative users of a managing entity to control which installations have access to the CDS System, and the timeframe during which that access is available; the Publishing section of the Console allows users to create and manage rule and value-set content; the Organization Subscription Management section of the Console allows organizational directors to control the available and default subscriptions for providers within their organizations; and the Provider Subscription Management section of the Console allows providers using the CDS-enabled Electronic Health Records (EHR) software to control the rules to which they subscribe.

CDS Server

The CDS Server is a stateless rule-processing server designed to service rule evaluation requests made by users as part of their workflow through a proprietary EHR application, and route them to the appropriate rule processing agent. As part of the workflow process, each EHR application makes calls to the server on behalf of a user.

When a call to evaluate rules is made, the CDS Server determines which rules need to be evaluated by communicating with the CDS Manager. The resulting rules are then grouped according to the rule processing agent that will perform the actual evaluation, and the call is passed to each rule agent. The results of all the agent calls are then grouped into a single set of recommendations and returned to the caller.

Rule Caching

Preferably, in order to avoid excessive calls to the CDS Manager, the set of rules that need to be evaluated for a particular provider and organization is cached in the CDS Server. This cache is transparently maintained whenever the subscription information or rule content is changed in the CDS Manager. The cache is also refreshed on a daily basis, because the set of rules to be evaluated can be different based on the effective timeframes for subscriptions and rule content.

The Notifier Service is responsible for distributing change notifications from the CDS Manager to the various rule servers that actually perform the evaluations. Whenever a rule server starts, it calls the CDS Manager to register itself as an active rule server, and provides an endpoint that the Notifier Service can use to communicate changes coming from the CDS Manager.

Common Rule Engine

The CDS System further includes a Common Rule Engine, which is responsible for actually evaluating the rules for a particular patient. The patient's information is provided as input to the evaluation call. The rule engine evaluates the criteria for each applicable rule in terms of the patient information, and if necessary, constructs recommendations with specific suggestions to return to the caller.

In some preferred implementations, the Common Rule Engine uses an extended rule definition format (Common Rule Engine Format (CREF)) that is based on Health Quality Measures Format (HQMF), but has been modified to support specific functionality required by the CDS System, such as, for example, rule parameterization, as described in more detail hereinbelow.

CDS Aggregator

The CDS System further includes a CDS Aggregator, which is responsible for tracking the recommendations for each patient and provider, as well as the dispositions of each provider that determine the status of each recommendation. The CDS Aggregator also tracks the history of each recommendation received for a patient, and audits operations on the recommendations such as viewing a recommendation, changing a status of a recommendation, or making a comment regarding a recommendation.

Coordination of the recommendations is preferably accomplished by comparison of a suggestion type (missing data or out-of-range), code set, and code of each recommendation. For example, if a recommendation is determined to be equivalent to another recommendation, it can be collapsed into the equivalent recommendation and the source can be listed as an additional source for the recommendation.

Additionally, the aggregator might determine that two recommendations should be grouped when they are similar. For example, one rule might recommend a patient be prescribed a specific class of drug, while another might recommend that a specific drug in that class be used, and a third might specify the same drug but with different dosage details (e.g., more complete, differing values). In some preferred implementations, the aggregator will consolidate this into one actionable recommendation with the more detailed options only visible upon further processing in concert with user input.

In at least some preferred implementations, prior recommendation dispositions might be used by the aggregator to suppress or modify presentation of new related recommendations. For example, a rule may frequently generate a recommendation for prescribing "asprin", while the same rule or another generates a recommendation for prescribing "1 mg Bayer asprin tablet taken with meals three times daily". In at least some preferred implementations, a user may be able to specify which they prefer. Alternatively, the rule may only generate the first recommendation and the user might add the second for themselves when they define a disposition (as described in more detail hereinbelow).

Further, the CDS Aggregator is capable of storing comments about each recommendation from each user of the software. These comments are made available as part of the information returned from the CDS Aggregator when a patient's recommendations are retrieved.

Timeframes

A Timeframe represents a date range during which a particular component or feature of the system is active. Most components have associated timeframes. For example, a rule definition has an associated timeframe, specifying the period of time during which the rule definition is active.

All timeframes have a start date, which may be any point in the past, present, or future. By specifying a future start date, changes can be configured to take effect at such future date. In addition, timeframes may or may not have an ending date. If no ending date is specified, the component or feature remains effective indefinitely.

Preferably, for components that depend on each other, when both components have a timeframe, the system ensures that the timeframe for the object being referenced encompasses the timeframe for the referencing object. For example, if an organization's timeframe is from Jan. 1, 2010 through Dec. 31, 2010, all providers in that organization preferably must have a timeframe that begins no earlier than Jan. 21, 2010, and ends no later than Dec. 31, 2010. For timeframes with no ending date, referencing objects are allowed to have an unspecified ending date as well.

Installation

As noted hereinabove, an installation represents a software site that will use a CDS System. Each installation preferably includes a unique identifier, which is preferably used to provide a unique identifier-space for CDS-external identifiers such as application-specific organization or provider IDs.

Organizations

As noted hereinabove, an organization represents the levels of the organizational hierarchy of an organization using the CDS System. Each organization may have any number of child organizations, but only one organization is required to use the system.

In addition to a CDS-generated identifier, each organization can specify an Installation ID and an External ID that is used to map the organization to a concept in the applications that will use the CDS System. Preferably, an External ID must be unique within the Installation ID for all organizations.

Organizational hierarchies are used to provide levels of control over the subscriptions offered to providers using the CDS System. For purposes of the CDS System, an organizational hierarchy does not necessarily need to completely mimic the organizational hierarchy of consumer applications. Rather, the CDS System only needs to represent enough of the structure to provide the level of subscription control that is needed for a consumer.

Providers

As noted hereinabove, a provider represents a medical care practitioner that can use a software application that communicates with the CDS System to provide real-time care recommendations.

As with organizations, providers have a CDS-generated ID, as well as an optional external ID. If specified, the external ID must be unique within the installation.

Each provider can be associated with any number of organizations, but each organization must not be a child organization of any other organization with which the provider is associated. This prevents ambiguity when applying subscription rules based on the organizational hierarchy for the provider.

Each provider may also be associated with any number of specialties. A specialty represents a specific medical field for use in describing the type of medicine a particular provider practices, as well as the field that is appropriate for a particular rule. Preferably, each specialty of a provider is assigned a priority in order to enable resolution of potential ambiguity when resolving subscriptions for multiple specialties.

Rule subscriptions can be organized by specialty, allowing a provider to easily identify rules in which they would be most interested.

In addition to the CDS-generated identifiers, specialties can be assigned an external ID per installation, or they can be associated directly by name.

Rules

A rule represents the basic unit of decision processing logic within the CDS System. The CDS manager can support any number of rule definitions. Each rule defines a timeframe during which the rule is effective.

Each rule may have any number of versions defined. Each version also specifies an effective timeframe. Subscriptions to a rule may be based on the rule itself, or they may be based on a specific version of the rule. If the subscription is to the rule, the most current version of the rule is used when the rule is evaluated.

In addition, the actual content of the rule may be changed within each version. When changes are made, an effective timeframe can be specified for such changes. This allows the CDS System to provide support for both versioned and effective-dated changes.

Each rule is allowed to specify any number of associated parties. Preferably, each party is an author, sponsor, or source, allowing the origin of the rule to be documented and presented as part of the generated recommendation.

Each rule is also allowed to specify any number of associated references. Each reference provides supporting evidence that will be presented as part of the generated recommendation. Each reference may also provide a link to more information.

Each rule can define any number of parameters which can be used in the definition of the rule to provide control over the rule evaluation, as well as the generation of the resulting recommendation. Each rule parameter specifies a default value as part of the rule definition, and can be provided on a per-patient or per-provider basis as part of rule evaluation.

Rule Sets

A rule set defines a group of rules and is used to organize the available rules in the CDS System. The CDS Manager can support any number of rule sets. Each rule set defines a timeframe during which the rule set is effective.

As with rules, each rule set may have any number of versions, each with an effective timeframe. Each version of the rule set is allowed to specify any number of rules that are part of that rule set. Subscriptions to the rule set may be based on the rule set in general, or a specific version of the rule set. This allows the CDS System to provide support for both versioned and effective-dated changes.

Rule Agent

A rule agent represents a processing agent capable of evaluating rules for the CDS System. The Common Rule Engine provides this functionality for rules authored in the native CDS rule format. Other rule agents can be plugged in to the CDS System, allowing third party processors to provide rule evaluation capabilities to CDS consumers. Each rule agent indicates which rules it is capable of processing.

Subscriptions

A subscription defines the set of rules that will be evaluated for a given provider and organization. Subscriptions are defined with an effective timeframe, and can be specified at any level of the organizational hierarchy, associated with any specialty, or specified at the provider level. For example, a subscription can be specified for all providers of a particular organization, or for all providers of a particular organization in a particular specialty.

Subscriptions can comprise rule sets, or specific rules. In each case, the subscription can be to a specific version of the rule set or rule (a specified subscription), or the subscription may be non-versioned, in which case the current version of the rule set or rule is used (a current subscription).

Subscriptions are built from the available rules for an organization. Each organization is allowed to specify the set of rules that are available. Each level of the organizational hierarchy can specify the availability of any number of rule sets and rules. Rule set and rule availability is inherited through each level of the organizational hierarchy.

Availability of a rule set or rule at an organization is specified with an effective timeframe, and an enabled flag is utilized to indicate whether or not that rule set or rule is available to that organization and its children, recursively. In this way, rule sets and rules can be made available or excluded at any level of a hierarchy.

As with subscriptions, rule availability can be specified, meaning that only a particular version of the rule or rule set is available, or current, meaning that all versions of the rule or rule set are available. Preferably, once a rule or rule set is made available using a specified version, it cannot be reverted to unspecified by a child organization. In such implementations, this means that if multiple versions of a rule must be available within an organization, then the version must not be specified as part of the availability.

Once available rule sets and rules are defined, subscriptions can be created to those rules at any level of the organizational hierarchy. Subscriptions can be defined on rule sets or specific rules, and can be defined for an organization, specialty, or provider.

In preferred implementations, subscriptions defined for an organization are inherited by all the children of that organization, recursively, and apply to all providers associated with that organization, or any of its children, recursively. Additionally, subscriptions defined for a specialty preferably apply to all providers with that specialty associated with that organization, or any of its children, recursively. Specialty subscriptions can preferably override subscriptions inherited from a parent organization (this would include potentially disabling an inherited subscription or changing a mandatory setting). Preferably, rule subscriptions can override rules included from a rule set subscription.

As noted above, rule or rule set subscriptions can be specified, meaning that the subscription is to a specific version of the rule or rule set, or current, meaning the subscription is to the current version of the rule or rule set. Preferably, in order for a subscription to be current, the rule or rule set involved must be current as well. If the version for a rule or rule set is specified in the availability for the organization, subscription to that rule or rule set can only be made to the specified version. Similarly, if the subscription for an organization or specialty is specified, only that version of the rule or rule set may be subscribed to by child organizations and associated providers.

In addition to the subscriptions inherited based on specialty and position within the organizational hierarchy, providers can subscribe to specific rule sets and rules, so long as those rules are available within the organization. Provider-level subscriptions can override inherited subscriptions, with the exception that a provider cannot opt-out of a mandatory subscription (although, in at least some implementations, specialty-level subscriptions can override mandatory organization-level subscriptions).

Preferably, when changes are made that would impact a provider's subscription, the CDS Manager will generate a provider notification to describe the nature and potential impact of the change. These notifications are made available by the CDS Manager and the CDS Server. Provider notifications will remain on file for a provider until they are acknowledged.

Users

A user in the CDS System is any person who is authorized to use the various features of the CDS System. Users can play a variety of roles within the CDS System. As described in more detail hereinbelow, these roles include an administrator role, which is a managing entity user responsible for maintaining rule content, managing installations, and maintaining security and licensing information for managing entity software clients; a publisher role, which pertains to any user responsible for maintaining content within the CDS System; a director role, which is a client user responsible for maintaining the organizational hierarchy for the client, as well as the available rules and default subscription information for each organization and/or specialty; a provider role, which is a care provider using the system to manage the set of rules in their subscription, as well as maintain rule parameters; and an end-user role, which is a client user performing rule evaluation for a specific provider, organization, and patient, as well as retrieving the resulting recommendations, and maintaining recommendation status and/or comments.

In order to perform any of these roles, a user must be given authorization based on their access to the particular area of the system, as well as their position within the hierarchy of the organization. Note that these roles may be played by the same actual user in different contexts. For example, a client user using proprietary EHR software may be playing a provider role to maintain their subscription information, and an end-user role to perform the actual evaluation calls as part of their workflow.

Preferably, a user management service provides various interfaces for finding and authenticating users, and determining what access they have within the CDS System, as well as their associated provider and organization information.

Value Sets

A value set is a set of clinical codes grouped together to form a concept used within rule definitions to define the criteria for a specific condition to be met. For example, a particular value set may contain all the ICD-9 codes for a diagnosis of Diabetes Mellitus. Rather than explicitly listing the codes in the rule definition, the rule may simply reference the particular value set, and the CDS Server will manage expansion of the value set to its constituent codes during evaluation of the rule.

Exemplary Systems

FIGS. 1-4 illustrate exemplary architecture for CDS Systems. The architecture can be characterized as including components that reside in three potential physical partitions: client infrastructure, managing entity infrastructure, and managing entity or client infrastructure.

Exemplary Systems—Managing Entity Infrastructure

Preferably, the main components of the CDS System reside within managing entity infrastructure.

A first of these components is the CDS Manager, which as described hereinabove is a centralized repository for the storage and management of CDS content, including rules and value sets, as well as subscriptions by organizations and providers to that content. FIGS. 1-4 all illustrate exemplary systems in which a CDS Manager resides within managing entity infrastructure.

As illustrated in FIG. 1, these components preferably further include a manager repository, which is a database containing the information managed by the CDS Manager. Preferably, the manager repository does not store patient-specific information of any kind. The rule definitions are all defined to act on patient data in the abstract, and no patient information is ever provided in any call to the CDS Manager.

Additionally, these components preferably still further include, as illustrated in FIG. 1: a CDS Console comprises one or more websites that expose user-interfaces for managing content and subscriptions in the CDS Manager; a CDS Notifier Service, which is responsible for notifying the CDS Service whenever changes are made to the content or subscription information contained in the CDS Manager; a User Management Service (UMS), which is an authorization service used by the CDS Manager to authenticate users and determine access rights to content and subscription information; a User Management Portal (UMP), which is a website that exposes user-interfaces for managing users and their associated organizations, providers, and access rights; and a User Management Portal Database, which stores the information managed by the User Management Portal.

In order to model subscription information for providers and organizations running proprietary (which may or may not be provided by the managing entity) EHR software, the CDS Manager preferably maintains some of the same information that is present in the User Management Portal. To manage this duplication, the CDS System preferably synchronizes data with the UMP. This process preferably occurs both on-demand, as required to satisfy requests made to the CDS Manager, as well as nightly to ensure timely and accurate information is present in the CDS Manager. The nightly synchronization process is performed by a CDS User Manager Sync.

Thus, in some preferred implementations, a CDS System includes its own user management functionality (as illustrated in FIG. 1). However, in at least some other implementations, the CDS System relies on user management functionality exposed by one or more other portals, services, or platforms (such as an "auth" platform illustrated in FIG. 2).

Exemplary Systems—Client or Managing Entity Infrastructure

Figure 2:
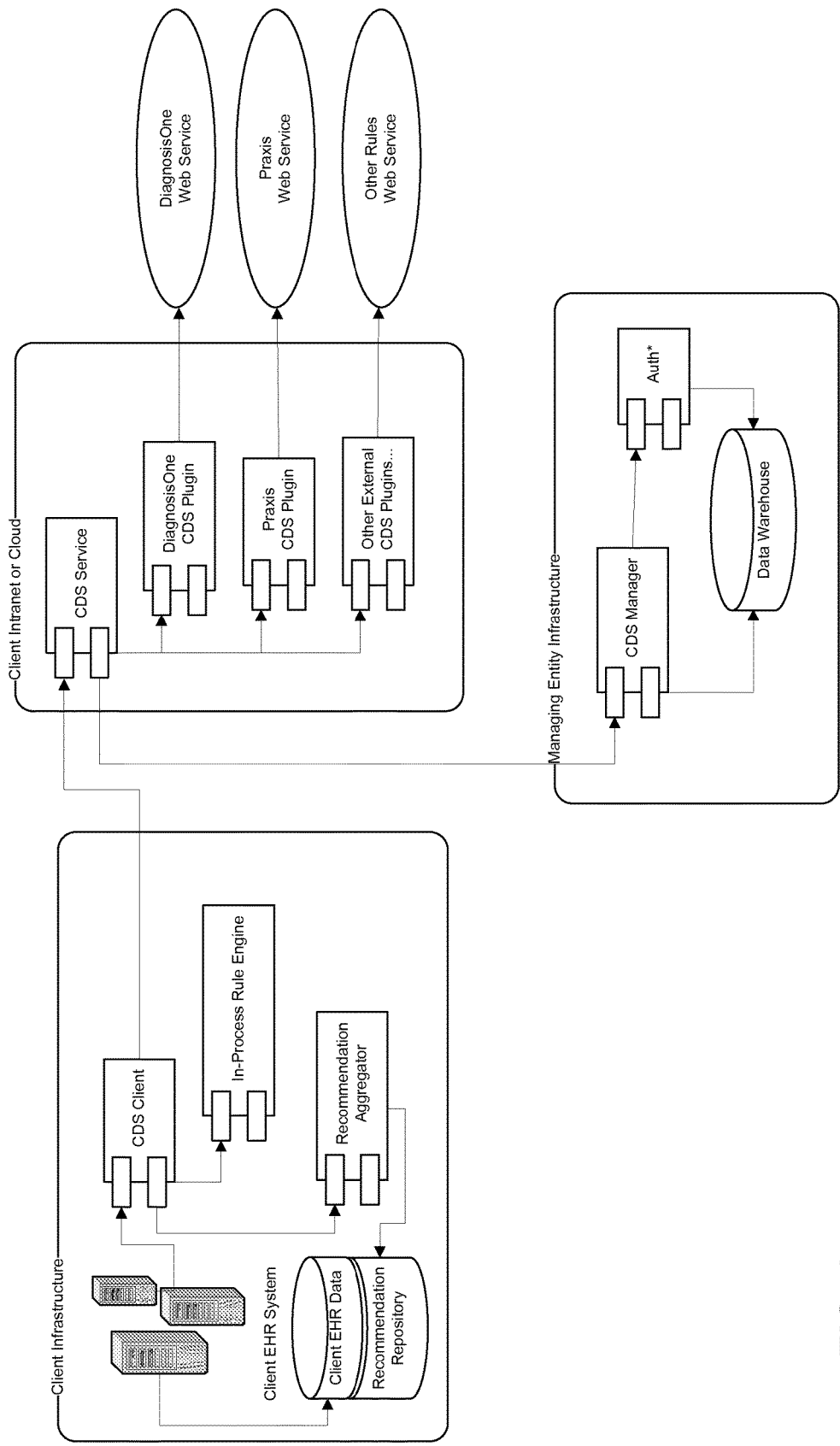
Figure 3:
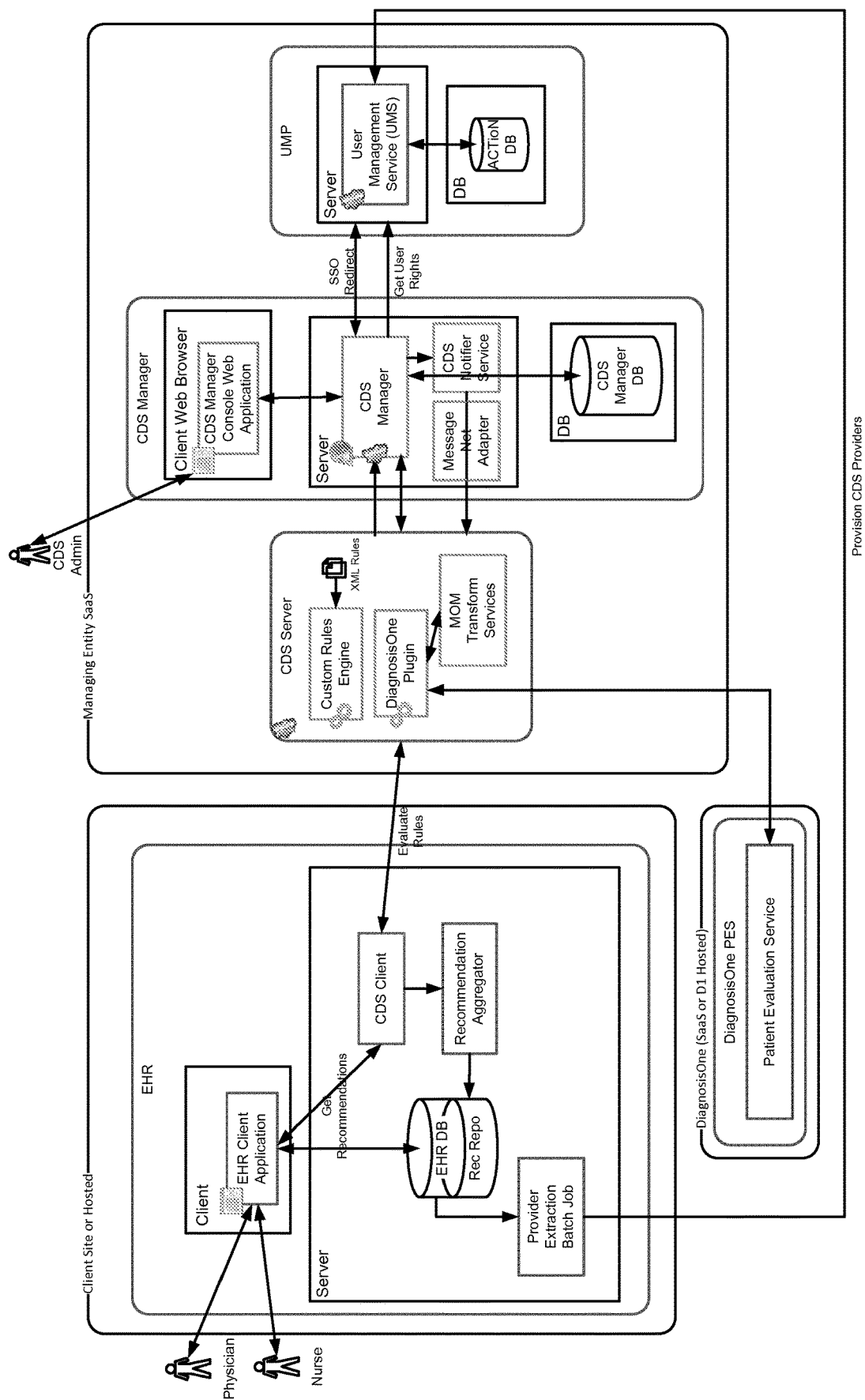
Figure 4:
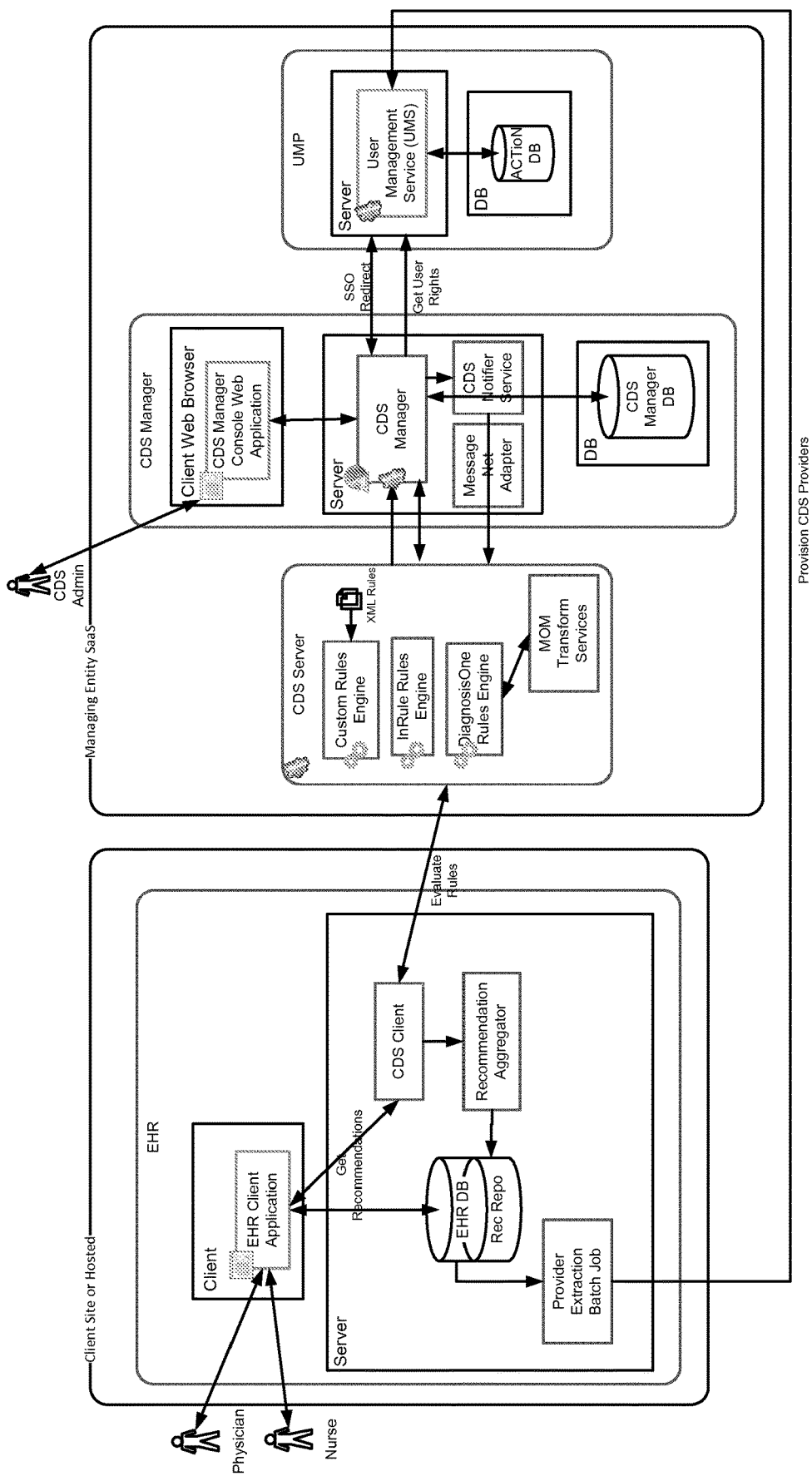

Preferably, a CDS evaluation engine is designed to be able to be hosted by clients as part of client infrastructure (as illustrated in FIGS. 1-2), or deployed alongside the CDS Manager within managing entity infrastructure (as illustrated in FIGS. 3-4). Preferably, the following components are configured to allow for such optional deployment.

A CDS Service, or Server, exposes the primary rule evaluation interface, and routes the evaluation requests to the appropriate rule-processing agent for the actual evaluation. The results of the evaluation from each agent are optionally combined into a single response and returned to the caller.

The CDS Service maintains a cache of the rules to be evaluated for each provider and organization combination. If this information is not present in the service cache, the CDS Manager is contacted to obtain the subscription information, as well as actual rule content.

Preferably, the CDS Service does not store the results of any evaluation. Each call is self-contained, and the results are returned immediately. In addition, if a call to the CDS Manager is required, no patient information is included in such a call, only provider and organization information is passed on to the CDS Manager. Alternatively, in at least some implementations, a copy of certain elements from each evaluation is retained for processing in the aggregate at a central system (a state-full version). This might be utilized, for example, to build population reporting capability.

A CDS Common Rule Engine (CRE) is a native rule engine for the CDS System responsible for evaluating rules defined in the Common Rule Engine Format (CREF). Rules defined in this format are stored in the CDS Manager Repository, and can be evaluated by the CRE without the need to contact any external services.

In addition to the native rule engine, the CDS System is preferably designed to allow for any number of external rule-processing agents to be added. Rules for these plug-ins are modeled within the CDS Manager, but the actual rule definitions are external, and the appropriate external rule-processing agent must be contacted to perform the actual evaluation.

Exemplary Systems—Client Infrastructure

Client components of the CDS System facilitate the integration of CDS functionality within proprietary EHR software. These components are preferably deployed as part of the EHR system within the client infrastructure.

These components include a CDS Client, which manages communication with the CDS Service, and coordinates reporting the results of the evaluation to another of these components, a Recommendation Aggregator. The CDS Client is the primary interface that integrating EHRs use to access CDS System functionality. In at least some implementations, however, the CDS client is configured to communicate directly with an in-process rule engine, as illustrated in FIG. 2, which is configured to perform in-process rule evaluations for at least some rules.

The Recommendation Aggregator is responsible for combining recommendations returned from multiple sources in to a single list of recommendations for a given patient and/or provider combination, and preferably detects and processes multiple related recommendations. For example, prior recommendations, dispositions and concurrent related recommendations might cause special system behavior such as the suppression of recommendation presentation or aggregate presentation. Preferably, such system behavior optimizes user interactions (workflow impacts). The Recommendation Aggregator preferably allows providers to ignore or address recommendations either individually, or based on the type of recommendation.

These components still further include a Recommendation Repository, which is the database that actually stores recommendation information for patients. The structures are all contained within a single schema (CDS), allowing the Recommendation Aggregator to be deployed in a separate database, or within the same database as the integrating EHR.

Language Support for Real Time Functionality

In one or more preferred implementations, a CDS System provides, in addition to clinical quality reporting, real time clinical decision support. Preferably, a CDS System enables an EHR system to provide accurate and meaningful clinical decision support on a real-time basis.

For example, a CDS System preferably provides the ability to evaluate patient information for triggers that will result in recommendations being returned to the provider at the point-of-care.

Because the system is used during actual provider workflows, it is desirable to reduce response-time. To reduce overall response-time, the system preferably allows for control over the amount of information that must be provided (e.g., to a rule evaluation engine) in order to perform a rule evaluation. Preferably, rule content is defined in such a way that only the minimum set of data required to perform an effective evaluation of the rules to which the provider is subscribed must be sent (e.g., to a rule evaluation engine).

Response-time is also be affected by load. As such, the system preferably is capable of scaling out to support potential load, and most preferably is capable of scaling out indefinitely. To enable this scalability, an individual engine instance itself is preferably stateless, and rule content does not hinge on any assumptions or dependencies on the availability of data. All access to patient information is preferably through a controlled and system-understood mechanism to allow the system to ensure scalability and reliability of the resulting recommendations.

In one or more preferred implementations, a language having certain desirable characteristics is utilized to facilitate a real-time CDS System.

Language Characteristics—Completeness

In order to allow for the expression of arbitrarily complex rules, the language preferably supports a full complement of operators to deal with patient information. As patient information can be characterized as sets of different types of values, the available operations preferably include database-like set operations, including selection, restriction, union, etc. In addition, a complete set of scalar operations including relative comparison, basic arithmetic, and logical operations is preferably available.

In addition, the language preferably supports the addition of new operations without impacting existing rule definitions, or requiring language definition changes.

Language Characteristics—Orthogonality

In language design, "orthogonality" refers to the relative independence of language concepts, and directly impacts both the simplicity and power of the resulting language. Preferably, the number of concepts in the language is as few as possible, and operations available are as broadly applicable as possible.

Language Characteristics—Missing Information

Preferably, the system is able to deal with missing information easily and gracefully. For example, if a rule requires a patient's age in order to trigger, the logic preferably is able to deal with the possibility that the patient information does not include a birth date or age. Rather than throw an error, or require the content developer to handle the case explicitly, the data model is preferably defined to allow the expression to be evaluated, it simply results in a null, rather than an actual value.

Language Characteristics—Implementation/Translation

The language is preferably designed in such a way that building execution and translation functionality based on the language is as simple as possible. To achieve this, rather than providing a syntax, which would require the associated compiler to be developed, the language preferably is defined at the Abstract Syntax Tree (AST) level. In a traditional language, the AST is the result of the lexical analysis and parsing phases of compilation. By defining the language at this level, development efforts can be concentrated directly on the execution engine itself.

This approach lends itself well to implementing execution engines, translation engines (e.g. to translate the rule logic directly to a database language such as SQL), and visual designers for the language.

Language Characteristics—Optimization

In order to guarantee the ability to optimize rule definitions, the engine is preferably defined to be strictly functional. No operations are permitted to change the state of any object within the execution engine. This allows the engine to ensure that any rewrites it performs will have no unintended side-effects.

Language Characteristics—Data Independence

Preferably, to the extent possible, operations in the language are defined to operate on any type of data. For example, rather than defining an Age operation in such a way that it knows about the Patient object and its associated BirthDate property, a CalculateAge operation is preferably defined that simply takes a BirthDate as a value. A separate operation is used to retrieve the actual BirthDate value from the Patient object.

Language Characteristics—Flexibility

Because the goals of real-time decision support are more targeted to the individual provider-patient relationship, the system preferably provides the ability to allow a provider to customize recommendation feedback from the rules engine without the need to modify the global rule definition. To accomplish this, the language definition preferably includes the ability to provide parameters as part of the execution context. These parameters are preferably available as data within the rule definition, and can be used to tailor the recommendation output, or customize whether a recommendation is returned.

Common Rule Engine Format (CREF) Language

Common Rule Engine Format (CREF) language represents an exemplary language in accordance with one or more preferred implementations developed in accordance with the above-described characteristics.

CREF Language—Data Model

A value in the CREF language represents a piece of data. All values are of some type, which designates what operations can be performed on the value. There are three categories of types in the CREF language: scalar types, which are types representing simple values such as integers, strings, and dates; structured types, which are types representing composite values comprising sets of named properties, each of which is another value; and lists, which are types representing lists of values of any type.

Scalar types allow for the representation of simple, atomic types, such as integers. For example, the value 5 is a value of type Integer, meaning that it can be used in operations that require integer-valued input, such as addition or comparison. The CREF language supports the following built-in scalar types: Boolean, for the logical values true and false; Integer, for integer numbers, represented as a standard 32-bit signed integer; Decimal, for real numbers, represented as a scaled integer (similar or identical to the .NET Decimal structure); DateTime, for date and time values (similar or identical to the .NET Decimal structure); and String, for character strings.

Structured types allow for the representation of composite types such as a Patient or Encounter. Structured types comprise a set of named properties, each of which are of some type, and may have a value of that type.

Structured values are of the same structured type if they have the same set of named properties, and those properties are of the same type.

To model patient medical information, the CREF language supports the following built-in structured types: CodedValueType; DateRange: Patient; Person; Encounter; Allergy; Problem; Result; Immunization; Medication; VitalSignObservation; Procedure; PlanOfCare; FamilyHistory; and SocialHistory.

List types allow for the representation of lists of values of some type. For example, a list of Encounter values (a composite value) may be used to represent the set of encounters for a patient.

CREF Language—Language Elements

The CREF language is specified at the Abstract Syntax Tree level. Whereas a traditional language would have syntax and require the overhead of parsing and compiling, the CREF specification allows expressions to be represented directly. This is accomplished using an XML representation of the structure of the expression. This XML representation is actually a XAML serialization of instances of the classes that provide the actual implementation of the rule logic. Each language element is represented by a named element in the XML document, with the attributes of the element, if any, represented as XML attributes. For example, the following fragment represents an expression for retrieving the current date: <ds:Today/>.

Arguments to operations are represented naturally using the hierarchical structure of the XML document. For example, FIG. 5 illustrates an expression for adding the integer values 2 and 2.

In this way, expressions of arbitrary complexity can be built up using the language elements available as part of the CREF language. These basic language elements include: rule; ClinicalAssertion; RequestExpression; and NamedExpression.

A rule is the primary container for rule definitions. A CREF rule is represented as a single XML document containing a XAML serialization of a DynamicRule instance. A clinical assertion is the mechanism used to represent the recommendations that will be returned as the result of evaluating the rule. A request expression is the mechanism for accessing patient data within the rule definition. A named expression is the mechanism for reusing and organizing expressions within a rule definition.

A Rule definition comprises: a Name, which is the name of the rule (e.g. NQF #13); a Description, which is a short description of the rule (e.g. Hypertension: Blood Pressure Measurement); a NamedExpressions, which is a set of named expressions, each of which has a unique Name and an Expression; a Criteria, which is a boolean-valued expression that is the primary triggering criteria for the rule (if the Criteria evaluates to true, the rule is triggered); a ClinicalAssertion, which is the definition of the recommendation to be returned if the rule is triggered.

FIG. 6 illustrates a simple rule definition with such basic elements.

CREF Language—Execution Model

All logic in the CREF language is represented as expressions. An expression may comprise any number of operations, so long as they are combined according to the rules for each operation. FIG. 7 illustrates exemplary fragments for value expressions for a scalar value and a list value.

The CREF language is strictly functional; no operation is allowed to change the values it is given. Expressions may return a value, but they may also return a null indicating the evaluation did not result in a value.

In general, operations are defined to result in null if any of their arguments are null. For example, the result of evaluating 2+null is null. In this way, missing information results in an unknown result. The exceptions to this rule are the logical operators, and the null-handling operators. The logical operators are defined using a 3VL truth table, in the same way that logical operations are defined in the presence of nulls in an ANSI-SQL standard database system. The null-handling operators, IsNull and Coalesce, are specifically designed to test for the presence of a value. IsNull is defined to return true if and only if its argument is null. Coalesce is defined to return the first non-null argument.

Evaluation takes place within an execution model that provides access to the data and parameters provided to the evaluation. Data is provided to the evaluation as a set of lists of structured values representing a patient's information. In order to be represented in the data set, a structured value must be a cacheable item. Cacheable items are structured values that must have the following properties defined: ID, a string value that uniquely identifies the structured value within a list of structured values of the same type; Codes, a list of CodedValueType values defining the medical codes that are applicable for the item; and Date, a date time defining the date/time of the item.

All access to a patient's information is performed through a RequestExpression, which has the following attributes: RequestType, the name of the structured type representing the requested information (e.g. Encounter, or Problem); Codes, an optional list of requested codes (if specified, each structured value in the result must have at least one of the codes in this list); DateRange, an optional date range (if specified, each structured value in the result must have a date that is greater than or equal to the starting date of the date range, and less than or equal to the ending date of the date range); IsInitial, which determines whether this request expression should be considered part of the initial data requirements for the rule evaluation.

Evaluation comprises two phases: a pre-processing phase, and an evaluation phase. The pre-processing phase is used to determine the initial data requirements for a rule. During this phase, any request expressions in the rule are analyzed to determine what data must be provided to the evaluation in order to successfully complete a rule evaluation. If the IsInitial attribute of the RequestExpression is set, the Codes and DateRange attributes of the request expression are evaluated to produce a request descriptor defining the data required by the rule. Parameter values may be accessed during this phase, but no patient data may be accessed, and attempting to do so will result in an error.

During the evaluation phase, the Criteria expression of the rule is evaluated. This expression is expected to return a Boolean value. If the expression returns true, the rule is considered triggered, and the ClinicalAssertion attribute of the rule is used to generate a recommendation to be returned.

Preferably, if the result of evaluating the Critieria expression for a rule is null, the rule is not considered triggered.

CREF Language—Operations

The CREF language defines the following operations: BinaryExpression, which is used to perform Logical (and, or, xor), Comparison (<, =, >, <=, >=, < >), and Arithmetic (+, −, *, /, mod, div, pow) binary operations; Condition, which evaluates a conditional (e.g., if x>3 then return x else return 0); Choice, which evaluates a series of conditionals; DateAdd, which performs date arithmetic; DateDiff, which computes the number of boundaries crossed between two dates; DatePart, which returns a component of a date; DateRange, which constructs a DateRange from two dates; DateRangeWithin, which constructs a DateRange from a date and an interval; ExpressionReference, which evaluates a named expression; FilterExpression, which filters a list of values based on a filter expression; IndexerExpression, which accesses the nth element of a list of values; IsNull, which tests an expression for null; ListExpression, which constructs a list from a list of expressions; LogicalConnective, which evaluates a series of logical expressions; ParameterExpression, which evaluates the value of a named parameter; PropertyExpression, which evaluates the value of a property; RequestExpression, which requests patient information; SortExpression, which returns the elements of a list in sorted order; Today, which returns today's date; UnaryExpression, which is used to perform Logical (Negation (not)), Arithmetic (Negation (−), Floor, Ceiling, Round), Exists, and List (First, Last, Count) unary operations; UnionExpression, which combines two lists; ValueExpression, which constructs a scalar value; and ValueSetExpression, which retrieves a list of medical codes from a terminology server.

Preferably, in addition to including these built-in operations, the CREF language is extensible.

CREF Language—Exemplary Fragments

FIGS. 8-13 include exemplary CREF language fragments illustrating various functionality of the CREF language in accordance with one or more preferred embodiments.

In particular, FIG. 8 includes exemplary fragments illustrating operations for adding two values, and finding a patient's age. FIG. 8 further includes a fragment illustrating use of a logical connective operation and a unary operation.

FIG. 9 illustrates data access expressions for determining systolic blood pressure measurements for the current day, and tobacco use within two years. Preferably, request expression is the sole means of accessing patient information. Preferably, this restricts patient data access to conjunctive queries, ensuring computability of dependencies and data requirements.

FIG. 10 illustrates the use of set-based operations. This example illustrates the use of a ValueSet Expression to identify a set of codes, the use of a FilterExpression to restrict the results of a RequestExpression, the use of the current context in the PropertyExpression in the Filter condition, and the use of Union to construct a combined list of codes.

FIG. 11 illustrates sorting using the CREF language. This example illustrates the use of aggregate operators, and the use of the SortExpression to order the results prior to use by the aggregate.

FIG. 12 illustrates parameterization utilizing the CREF language. Specifically. ScreeningMonths is utilized to provide the range of the data requested.

FIG. 13 illustrates the use of named expressions. Preferably, named expressions are used to provide organization and expression re-use within rule definitions. The first code segment in FIG. 13 illustrates the definition of a HasHypertension named expression, and the second code segment illustrates the use of an Expression Reference to reference such HasHypertension named expression in a LogicalConnective.

LISP Implementation

In one or more alternative implementations, the rule engine is implemented utilizing LISP syntax.

Exemplary Functionality

In one or more preferred implementations, by allowing for the programmatic description of required information, a system can send only the information that will actually be used by the content to which a provider is subscribed. This often significantly reduces the overall size of rule evaluation requests being sent by each provider. In aggregate, this can lead to a significant reduction in the resources required to perform real-time clinical decision support. In addition, because the mechanism is built into the content definition and the call-level interface, the request size can be tuned dynamically, if necessary.

Further, one or more preferred implementations described herein allow for customization of a care provider's experience. By allowing rule content to contain parameters for specific values, rather than making those hard-coded as part of the rule content, a provider is able to control whether a recommendation is triggered for a specific patient or practice. Preferably, this functionality is possible without creating a new version of the rule with the different value, which can lead to excessive administrative overhead in managing the additional content required for each permutation of values in each rule.

In preferred implementations utilizing the CREF language, because of the approach taken in CREF, e.g. because the format specifies logic at the functional level, there is no need for language syntax. This eliminates the need for lexical analysis, parsing, and compiling that might be required when using other syntax. In addition, the format preferably allows for rapid development of engine technologies such as the actual rule evaluation engine, rule translation, or visual content editors.

Exemplary Usage

Various exemplary usage scenarios and user roles for the CDS System will now be described.

Exemplary Usage—Point-of-Care

A primary usage scenario for the CDS System is the point-of-care evaluation request. As providers or other healthcare workers using an EHR enter patient data, the EHR triggers a rule evaluation request with the latest information for the patient.

The EHR integration preferably packages the patient's information and sends it in an evaluation request to the CDS Server. The server evaluates whatever rules are configured for the provider and return the results as a set (possibly empty) of recommendations.

These recommendations are processed by the CDS Aggregator and merged into the current set of active recommendations for the patient. The CDS Aggregator is responsible for eliminating duplicate recommendations, as well as applying the provider's disposition to the resulting recommendations. Once this processing is complete, the resulting set of active recommendations is returned to the EHR.

These recommendations are then displayed to the user within the EHR. The actual display of the recommendations is preferably determined by the integrating EHR.

Exemplary Usage—User Roles

As noted hereinabove, there are five roles that users typically play within the CDS System: CDS administrators; content publishers; organization directors; providers; and end-users.

CDS administrators are responsible for managing the set of installations available within the CDS System, as well as the set of rule agents available, and which rules each agent is capable of processing.

Content publishers are responsible for creating and maintaining the content available within the CDS System, including rule and value set definitions.

Organization directors are responsible for establishing the rules and rule sets available within an organization, as well as the mandatory and optional subscriptions for their organization. In addition, an organization director manages the organizational hierarchy for an organization, and providers within each level of the hierarchy.

Providers are responsible for managing their particular subscriptions within an organization. Each provider will inherit a default set of subscriptions based on their position within the organizational hierarchy, as well as their stated specialty. Beyond that, providers may opt-in to additional available rules, or opt-out of non-mandatory rules available at their organization.

"End-users" as used herein generally refers to client software users that use the rule evaluation and recommendation aggregation features of the CDS System. A particular provider is considered an end-user when performing a rule evaluation as part of their workflow in an EHR application.

Exemplary Usage—User Roles—CDS Administrator

A CDS administrator is responsible for managing the global configuration aspects of the CDS System. A CDS consumer must first be established as an existing installation with a valid subscription by a CDS administrator before the consumer can access the functionality provided by the CDS System.

A CDS administrator can perform the following functions within the CDS System: manage installations; manage specialties; manage rules and rule sets; and manage rule agents.

Installations are used within the CDS System to represent an organization or group of organizations that are authorized to use the system. Each installation corresponds with an installation of software at the client site. The ID of the installation is used to ensure the uniqueness of other external IDs referenced within the CDS System, so the installation should correspond with the container for the client. For example, if a client has multiple software installations within their organization, the possibility exists for two different providers or users within that software to have the same ID. To ensure that providers from both these systems can be represented uniquely within the CDS System, the client would be set up with multiple installations, one for each software installation in their organization.

In addition to specifying the ID-space for organizations and providers, the installation specifies the subscriptions associated with the installation. Each subscription specifies a root organization and a timeframe during which the subscription is active. The subscription for the root organization determines the overall subscription for that organization and all its sub-organizations, recursively.

Root organizations and the users that have access to them can only be maintained by CDS administrators.

The CDS System supports the configuration of any number of specialties. Each specialty can be used by organization administrators to specify subscriptions that should be associated with providers of that specialty. Specialties are defined with a timeframe in order to allow specialties to be introduced and removed as necessary.

Rule agents are used within the CDS System to represent a component of the system that is capable of evaluating rules. The CDS System can be configured with any number of rule agents. The default CDS System has a native rule agent called the Common Rule Engine which is capable of processing rules expressed in the Common Rule Engine Format.

Exemplary Scenarios—User Roles—Content Publisher

A content publisher is responsible for creating and maintaining the content exposed by the CDS Manager. The content includes the definitions of each rule that can be processed by the system, as well as the value sets used by those rule definitions.

Content publishers are responsible for managing the rules and rule sets that are globally available. Any rule or rule set defined in the CDS System will be available to organization directors for use in building the set of available rules and rule sets for their organization.

Content publishers are also responsible for managing the value sets exposed by the CDS Manager. As described hereinabove, rather than explicitly specifying the set of codes for a particular concept, rule definitions can reference a value set instead. This allows multiple rules to use the same value set without duplicating the codes defined in the value set. In addition, value sets can vary independent of the rule definitions that use them.

Exemplary Usage—User Roles—Organization Director

An organization director is responsible for managing all the configuration aspects of the CDS System for a particular organization. Each installation represented within the CDS System can have any number of organizations configured. Each organization can also have any number of sub-organizations, allowing the organizational hierarchy of the site to be represented in as much detail as necessary within the CDS System.

Rule availability and subscription management follows the organizational hierarchy. The organizational hierarchy is made up of a root organization, and any number of sub-organizations. Each sub-organization in turn can have any number of sub-organizations, recursively. In addition to the description of the hierarchy, each organization (or sub-organization) specifies the following information: name and description of the organization; timeframe during which the organization is active; the set of providers associated with the organization; the set of rule sets and rules available at the organization; the set of rule sets and rules that are part of the default subscription for the organization; and the set of rule sets and rules for each specialty that are part of the specialty subscriptions for the organization.

Due to the potential variability in the way specialties are represented within the various systems that will be calling the CDS System, specialties can be mapped to different external identifiers for each installation. Once the mapping is established, the application can use its native specialty identifier when communicating with the CDS System.

When a rule set or rule is made available at an organization, it is available for subscription by any provider associated with the organization, or any sub-organizations, recursively. Note that this means that the organizational hierarchy only needs to be represented as far as is necessary in order to capture the desired rule configuration for a particular organization. For example, an organization may actually have several departments within a particular site, but if all those departments make use of the same rule configuration, there is no need to model the departments within the CDS hierarchy. However, each organization level is allowed to override the availability of any rule sets or rules inherited from the parent organization.

Each user performing the role of organization director is assigned to a particular organization within the installation. The user can manage the configuration of their assigned organization, as well as any sub-organization, recursively. However, the user cannot see or manage organizations above them in the hierarchy.

The organization director can perform the following basic function within the CDS System: manage the organizational hierarchy; manage specialty mapping; manage rules and rule sets available at the organization, or any sub-organization; manage rule and rule set subscriptions at the organization, or any sub-organization; manage specialty subscriptions for the organization; manage the set of providers assigned to the organization; and manage the set of users assigned to the organization.

When a rule set or rule is made part of the default subscription for an organization, it becomes part of the default subscription for any provider associated with that organization, or any sub-organizations, recursively. If the subscription is marked mandatory, the provider may not opt-out of the subscription. Just as with rule availability, the default subscription for an organization can be overridden by sub-organizations.

In addition to the default subscription, each organization is allowed to specify a default specialty subscription for any number of specialties. When a rule set or rule is made part of the default specialty subscription for an organization, it becomes part of the default subscription for any provider with that specialty that is associated with that organization, or any sub-organizations, recursively. Again, the default specialty subscriptions for an organization can be overridden by sub-organizations.

A provider may be associated with any number of organizations, but each organization to which a provider belongs must not be a sub-organization of any other organization for the same provider. This restriction allows the rules for a provider to be determined unambiguously.

In some implementations, an end-user can similarly be associated with any number of organizations, but, just as with providers, each organization to which an end-user belongs must not be a sub-organization of any other organization for the same end-user.

Generally, a user within an organization may be associated with any number of organizations, but each organization to which a user belongs must not be a sub-organization of any other organization for the same user. Note that a particular user may play multiple roles within an organization. For example, a user may be both a provider and an organization director.

Exemplary Usage—User Roles—Provider

A provider can manage rule and rule set subscriptions through the CDS Console. The CDS Console preferably allows providers to configure the set of rules that will be evaluated for each patient they encounter. Each provider is associated with at least one organization, and that organization determines the rules that are available for that provider, as well as their default subscriptions.

Based on their position within the hierarchy of an organization, as well as their specialties, providers preferably automatically have one or more default subscriptions. In addition to such default subscriptions, a provider may opt-in to additional rules and rule sets available at their organization, as well as opt-out of non-mandatory subscriptions.

Organizations can configure each rule for providers in one of three ways. A first option is Opt-In, in which a rule is available to the provider, but they must explicitly subscribe to the rule in order to receive recommendations for the rule. A second option is Opt-Out, in which, by default, the provider is subscribed to the rule and will receive recommendations for it, but the provider has the option to unsubscribe for the rule if they do not wish to receive those recommendations. A third option is Mandatory, in which the provider is subscribed to the rule and does not have the option to unsubscribe.

Provider subscriptions can be established either as current or specified. For a current subscription, the subscription is established to a rule itself, and the CDS System will always use the most recent, available version of the rule to perform an evaluation. In contrast, for a specified subscription, the subscription is established to a specific version of the rule, and the CDS System will always use that version to perform the evaluation, even if newer versions are available.

Preferably, if a provider is subscribed to a rule and a new version of that rule is created, the provider receives a notification message. If the provider has a current subscription, the notification will state that rule evaluation requests will begin using the new version of the rule as of the effective date of the new version. If the provider has a specified subscription to an older version of the rule, the notification will state that a new version of the rule is available, and the provider can use the CDS Console to view and/or subscribe to the new version.

The CDS console includes a Manage Provider Subscriptions interface that enables a provider to manage their subscriptions. In order to access this interface, a user must first log in to CDS Console. FIG. 14 illustrates an exemplary login interface for a CDS console.

Upon logging in, a user clicks a Provider Subscriptions hyperlink to access the Manage Provider Subscriptions interface which lists the rules to which the user is subscribed including mandatory rules. FIG. 15 illustrates such Manage Provider Subscriptions interface.

The Manage Provider Subscriptions interface can be used to view, subscribe to, and control upgrades of clinical decision support rules. Furthermore, providers can use the Manage Provider Subscriptions interface to view the details associated with rules, subscribe to rules or remove subscriptions to rules, tag rules so that they are automatically updated when new rules are activated, lock in to specific versions of rules so that updates are not applied to those rules, and override the parameter values for rules.

The user can click "Show all available rules" to display a list of all the available rules to which the user is not currently subscribed. To show only subscribed rules, the user can click "Show my rules only".

To view the details for a given rule, a user clicks the plus sign to the left of the rule. When the details are visible, the plus sign turns to a minus sign. To collapse the rule details, the user clicks the minus sign.

FIG. 16 illustrates the display of details for a rule via the Manage Provider Subscriptions interface. Rule details include description details, regulatory information, recommendation information, rule parameters, and source information.

Description details include version information relating to the version of the rule to which the user is subscribed. As described hereinabove, a rule can have multiple versions. If a rule is updated, it is assigned a new version number. Unless locked to an earlier version of a subscribed rule, a user is automatically subscribed to the latest version of the rule when a new version of the rule is activated, and any parameter customizations are applied to the new version of the rule.

Regulatory information can specify a regulatory measure that the rule satisfies.

Recommendation information relates to the recommendation text that appears to the provider when diagnosing and treating patients.

Rule parameters indicate the parameter values used by the rule. These values can override default parameter values. Notably, if a rule does not have any parameters, the Rule Parameters group box does not appear, as is the case in FIG. 16.

Source information includes information relating to the activation date of the current version of the rule, evidence such as external references for the current version of the rule, authorship information, and sponsorship information.

Using the Manage Provider Subscriptions interface, a user may select the rules desired to be used when diagnosing and treating patients utilizing a "Subscribed" check box of the interface. That is, a user can check the box to indicate that they wish to subscribe to the rule, or uncheck the box to stop using the rule.

As noted above, a rule can have multiple versions. A user can automate CDS rule upgrades by accessing the description details for a rule. If automatic upgrades are not already activated, then the description details will provide a hyperlink allowing the user to indicate that they wish to enable automatic updates to the most current version of the rule, as illustrated in FIG. 17.

Alternatively, the user has the ability to lock in a specific version of a rule so that the rule is not upgraded to a new version when a new version of the rule is activated. To accomplish this, a user accesses description details for a rule. The description details will include a lock hyperlink allowing the user to indicate that they wish to lock to a particular version of the rule, as illustrated in FIG. 18. If multiple versions are available, non-current versions will preferably be displayed in an "other-versions" grouping, and a user will have the option of locking to any available version.

A rule can have multiple default parameters. A user has the ability to change a rule parameter so that it uses a user-specified value rather than the default value. The user can effect such a change via the Manage Provider Subscriptions interface. Specifically, for rules including parameters, a provider can preferably access rule details and input an override value for any rule parameter, as illustrated in FIG. 19.

Exemplary Usage—User Roles—End-User

The CDS end-user role is used to perform the real-time rule evaluation functions of the system, as well as the disposition and recommendation management functions in the CDS Aggregator.

An end-user can perform the following functions in the CDS System: manage rule parameters; view recommendations for a patient; manage recommendation dispositions; change recommendation status; and maintain recommendation comments and ratings.

All these functions are preferably performed at a client site as part of the functionality exposed by the CDS Aggregator.

Preferably, when changes are made to rule content, the CDS System will generate provider notifications to inform potentially impacted providers of the change.

When a new version is added to an existing rule, all providers with a current subscription to that rule will receive a notification indicating that a new version has been created, and their evaluations will begin using the new version as of the effective date of the version. For providers that have a specified subscription to a previous version of the rule, the system will issue a notification indicating that a new version of the rule is available as of the effective date of the version, but the specified version will continue to be used barring a change by the provider. For providers that have a current subscription, notifications will only be generated if the current version of the rule is the one that was changed.

Exemplary Usage—Managing Recommendations

The CDS System supports tracking a rich set of recommendations for patients in EHR applications. Recommendations can come from a variety of sources including batch processes that produce nightly recommendations, as well as real-time rule evaluations that produce immediate recommendations based on a current workflow within the EHR.

Preferably, all patient recommendations, and any operations performed on them, are tracked by the CDS Aggregator. As described hereinabove, the CDS Aggregator is responsible for detecting and processing related recommendations, as well as applying provider and user dispositions to recommendations.

In addition to a text description of the recommendation itself, each patient recommendation preferably contains a variety of information about the source of, and evidence for, the rule that generated the recommendation. This information can be displayed in different ways depending on how recommendations are retrieved and displayed in each EHR application.

In some preferred implementations, display of recommendations is configured to be directly actionable. For example, if a recommendation to prescribe a medication or order a lab is presented, in some preferred implementations, such recommendation is presented with a single click to act on the recommendation.

Each recommendation can be associated with a specific provider, or can be associated only with the patient. If a recommendation is associated with a provider, it is preferably only visible to that provider, or a user retrieving recommendations for a patient on behalf of that provider.

When a recommendation is generated based on a request to evaluate the rules for a specific patient and provider as part of the current workflow in an EHR application, any recommendations that are generated are automatically associated with the provider making the evaluation request.

Each recommendation tracks the rule source responsible for generating the recommendation. If multiple sources produce the same recommendation, or related recommendations, the CDS Aggregator preferably detects the duplication, or related nature, and combines the recommendations into a single recommendation. However, the CDS Aggregator preferably still keeps track of the fact that the recommendation came from multiple sources, and this information is made available when the recommendations are retrieved.

For example, if a provider is subscribed to two different rules that both produce the same or related recommendations, preferably only one recommendation will be returned, but it will list both rules as sources for the recommendation. In addition to the set of current recommendations, the CDS Aggregator preferably tracks the history for all recommendations that were received for a patient. When a new batch of recommendations is reported, the current recommendations for the patient are preferably moved to the history. Preferably, if a recommendation is reported as part of a batch recommendation process, and the same or a related recommendation appears in the result of a rule evaluation call, only one combined recommendation will be returned, listing both rule sources for the combined recommendation.

The CDS Aggregator also preferably audits any changes made to a recommendation while it is current.

Historical recommendations for a patient can be retrieved for a patient by requesting that history be included in the result. For historical retrieval, a date range, or a specific encounter can be provided. Historical recommendations preferably have one of 3 statuses: Replaced (RPL), No Longer Reporting (NLR), or Duplicate (DUP).

When a new set of recommendations is received, the aggregator preferably processes each recommendation. In some implementations, if a new recommendation is the same as an active recommendation for the patient, the existing recommendation is marked as "Replaced" and moved to the history. In some implementations, if a new recommendation is equivalent to any other new recommendation, the new recommendation is marked as "Duplicate" and moved to the history. In some implementations, any recommendation that was active, but is not part of the newly reported recommendations is marked as 'No Longer Reporting' and moved to the history. In at least some implementations, however, some of these steps would be inappropriate if the same rules are not always run, for example if different rules are run in batch and in real-time, promoting recommendations to "No Longer Reporting" might be inappropriate.

Once the recommendations are processed, dispositions for the provider and end-user reporting the recommendations are applied.

The CDS Aggregator supports tracking the disposition of each recommendation for a patient, not only for the patient directly, but for each potential user of the system. In this way, users can have different dispositions for the same recommendation.

For example, a provider may have already reviewed and addressed a particular recommendation, and so would indicate that through a disposition. That recommendation would no longer be visible to that provider. However, a nurse or other client user acting on behalf of the provider for the same patient would still see the same recommendation as active, until they take their own steps to address the recommendation.

In addition to applying for different users (or end-users), dispositions can apply at the following levels: Single-Recommendation, that is a disposition can be applied to a specific recommendation; Recommendation Type, that is a disposition can be applied to all recommendations of a specific code (e.g. LOINC 4548-4); and Rule, that is a disposition can be applied to all recommendations generated by a specific rule (e.g. NQF #13).

The CDS Aggregator supports specifying the disposition of a specific recommendation. In at least some implementations, each time recommendations are reported, each recommendation is considered a new and unique recommendation, so dispositions associated to specific recommendations are single-use only. They would not apply to a new recommendation generated by the same rule. In at least some implementations, however, when a new recommendation is received and is about to replace an existing one, the disposition of that existing recommendation might be "applied" to the new one. The user might be informed that the recommendation has been made again or the information may be suppressed based on the prior resolution. Preferably, user input is utilized to determine whether a new recommendation is suppressed based on a prior disposition. In preferred implementations, when a user makes a disposition, the user can mark the disposition as "permanent", or as valid only for the a specific instance of the recommendation.

The CDS Aggregator also supports specifying the disposition of all recommendations that contain suggestions that match based on the following criteria: Kind (Out-of-Range or Missing Data); CodeSet and Code (The coding for the suggestion, e.g. LOINC:4545-8); and Severity, which is optional, and represents the severity of the recommendation.

For example, if the severity is specified as part of the disposition, then the disposition will only match recommendations with the same severity as the disposition. This type of disposition is useful in scenarios where different rules result in the same type of recommendation.

Additionally, the CDS Aggregator supports specifying the disposition for all recommendations generated by a specific rule. As with the Recommendation Type dispositions, the Severity of the recommendation can be optionally specified.

Such Rule type dispositions are useful in scenarios where different rules would result in the same type of recommendation, but potentially for different reasons. For example, if a rule generated a recommendation, and the provider has already addressed it, if a separate rule generated the same type of recommendation, the recommendation would be visible because it was generated by a different rule.

Each disposition supports an optional disposition reason and comment, which allows users to provide more detailed information about the reason for a particular disposition. Disposition reasons provide a list of pre-defined reasons that can be selected. In addition, user-defined reasons can be created, allowing users to create lists of common reasons used when handling recommendations.

Disposition reasons are organized hierarchically, based on their reason code. The system-defined list of reasons makes up the root of the hierarchy: 100 (Recommendation accepted); 200 (Not clinically relevant); 300 (Patient refused for religious reasons); and 400 (Patient refused for personal reasons).

To create a new disposition reason, users must choose an existing disposition reason, and then provide the description for the new reason. If the chosen reason is a root disposition reason, the new reason is created as a sub-reason using the next available reason code. For example, to create a new disposition reason based on the Not clinically relevant reason, the user would choose reason ID 200, and provide the new description: Value is out of range for this patient. When the disposition is reported, the system will create a new reason ID with code 200.1, and the new description.

If the chosen reason is not a root disposition reason, the new reason is created as a peer. For example, if a user chose the new reason created above, 200.1, then the system would create a new reason with ID 200.2.

The root disposition reasons are system-defined so that quality reporting can be performed on disposition reasons. For this reason, it is important to create sub-reasons that are related to their parent reasons.

Recommendation dispositions also support expiration. A disposition can be configured to apply only through a specified expiration date using the Until property. Alternatively, a disposition can be configured to apply to a specific encounter. Once the expiration date is reached, or recommendations are reported for a different encounter, the disposition no longer applies.

In addition to tracking the recommendations and dispositions for a patient, the CDS Aggregator supports tracking comments and ratings for each user for each recommendation. This allows users of the CDS System to provide feedback on the quality or accuracy of a given recommendation.

Each recommendation can have an associated comment and rating for any number of users. This information is made available when the recommendations are retrieved from the CDS Aggregator.

Exemplary Usage—Parameters

The CDS System supports the ability to change the parameters of a rule based on the current patient or provider. For example, if the criteria for a rule states that patients within a particular population should have a mammogram once every 24 months, the provider has the option to change the criteria based on their preferences.

The configured parameter can be applied at the provider-level, in which case it would apply to all patients for that provider, or at the provider-patient-level, in which case it would apply only to a specific patient for that provider.

Note that this is only supported if the rule is defined with parameters. In this way, only variables that should be allowed to be changed based on provider preferences can actually be configured. If a guideline is such that a parameter should not be used, the rule definition will not expose the criteria in question as parameters.

Exemplary Data Structures

Figure 20A:
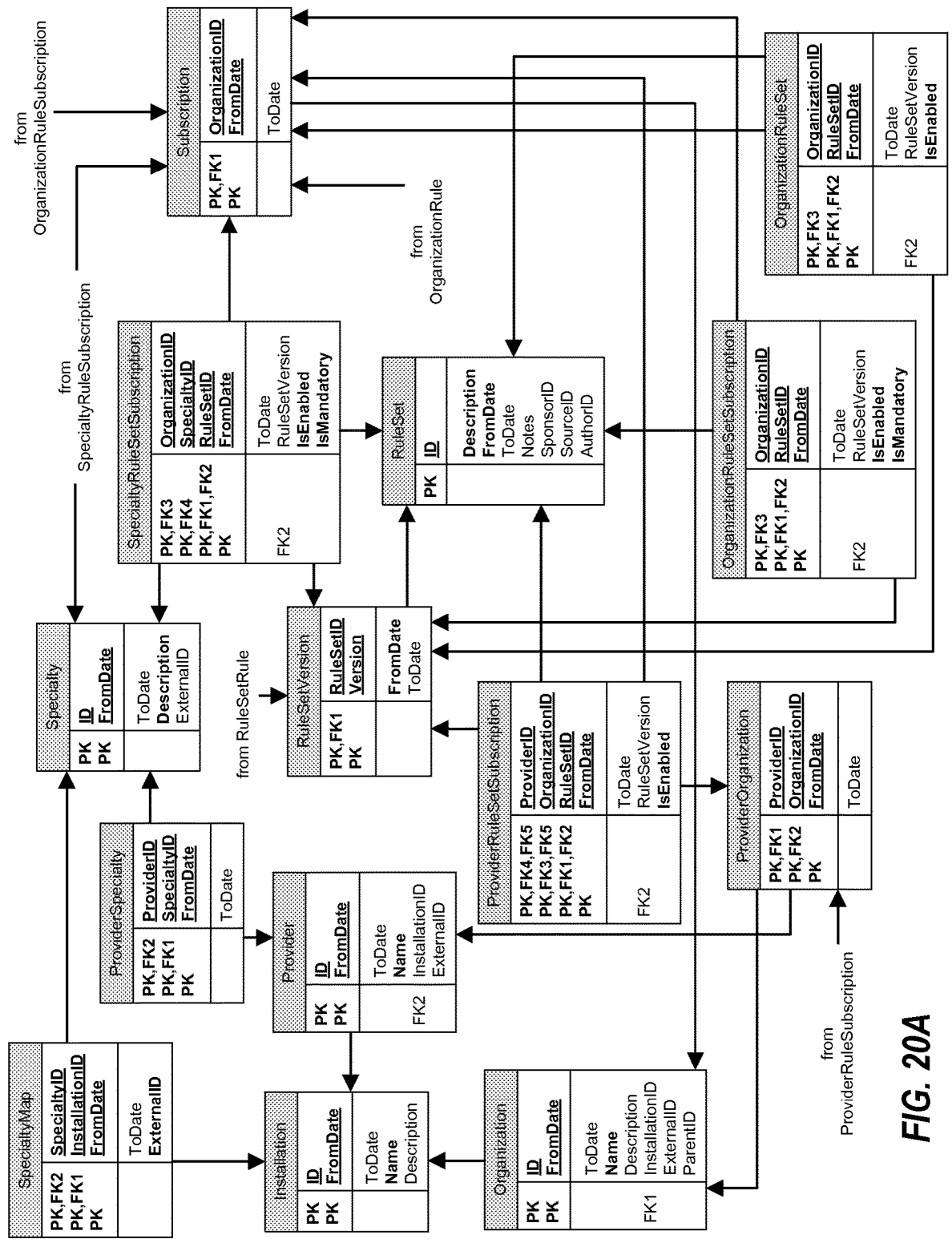
FIGS. 20A and 20B, taken jointly, are a block diagram of a data model for the manager structures of a clinical decision support system in accordance with one or more preferred embodiments of the present invention.
Figure 20B:
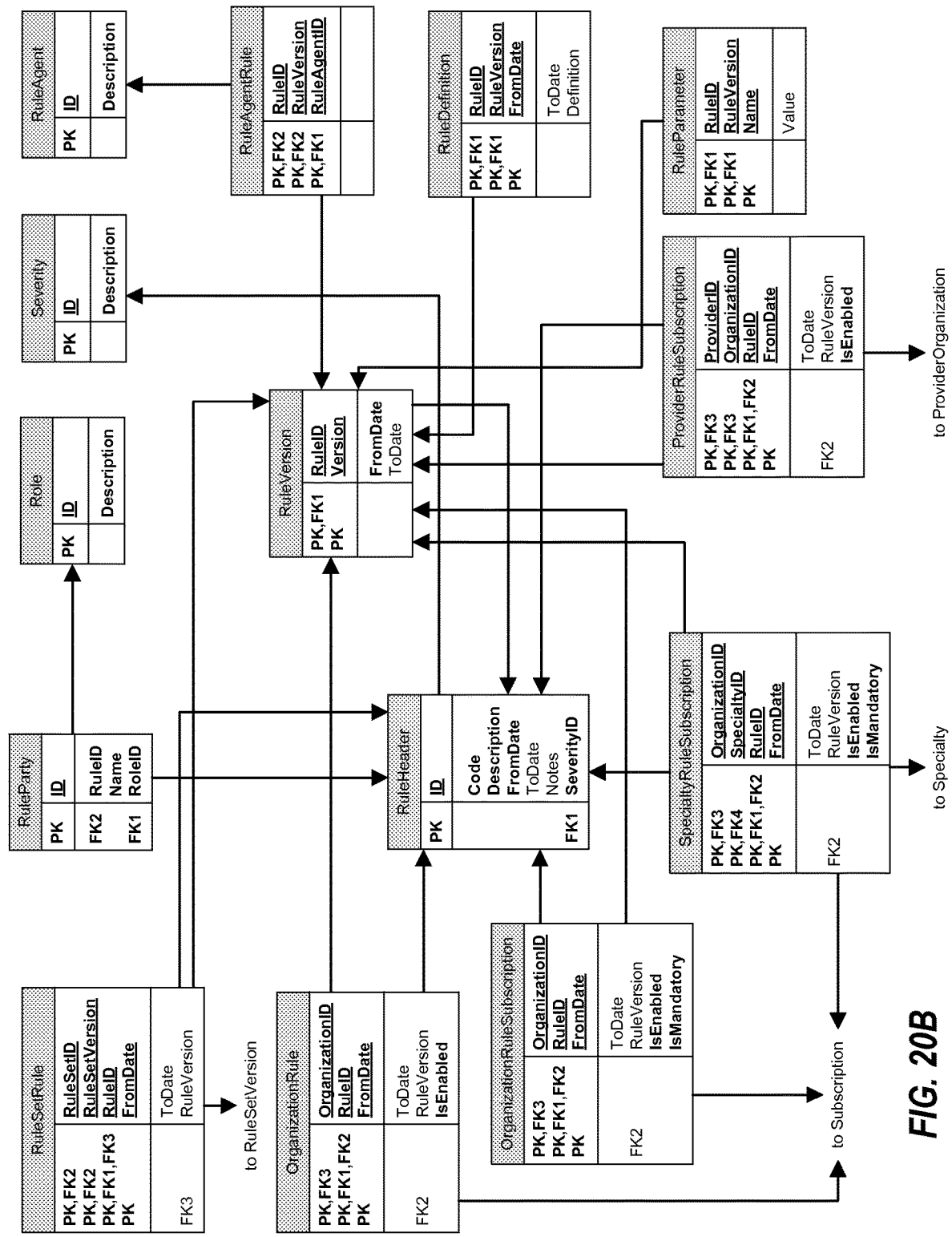
Figure 21A:
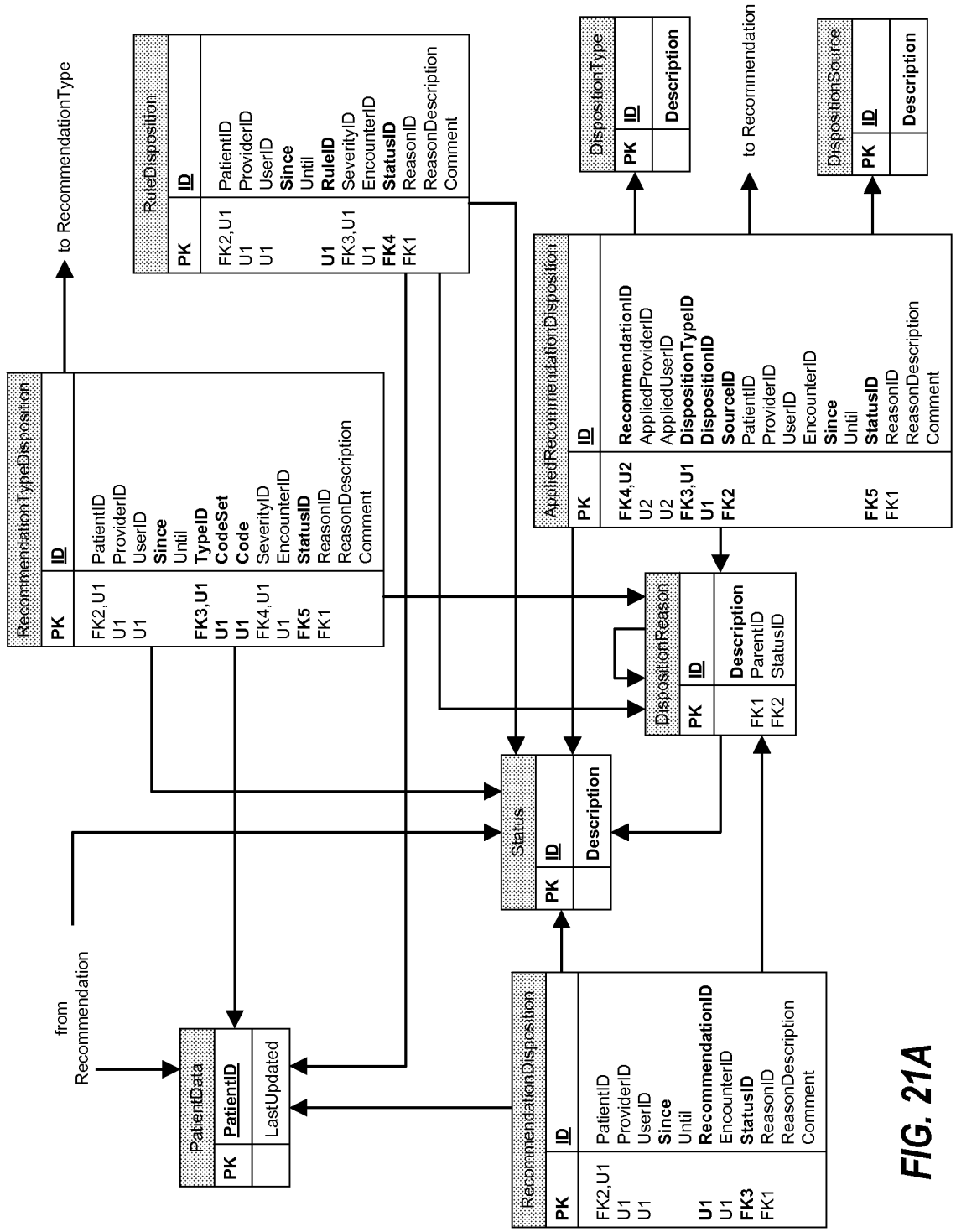
FIGS. 21A and 21B, taken jointly, are a block diagram of a data model for the aggregator structures of a clinical decision support system in accordance with one or more preferred embodiments of the present invention.
Figure 21B:
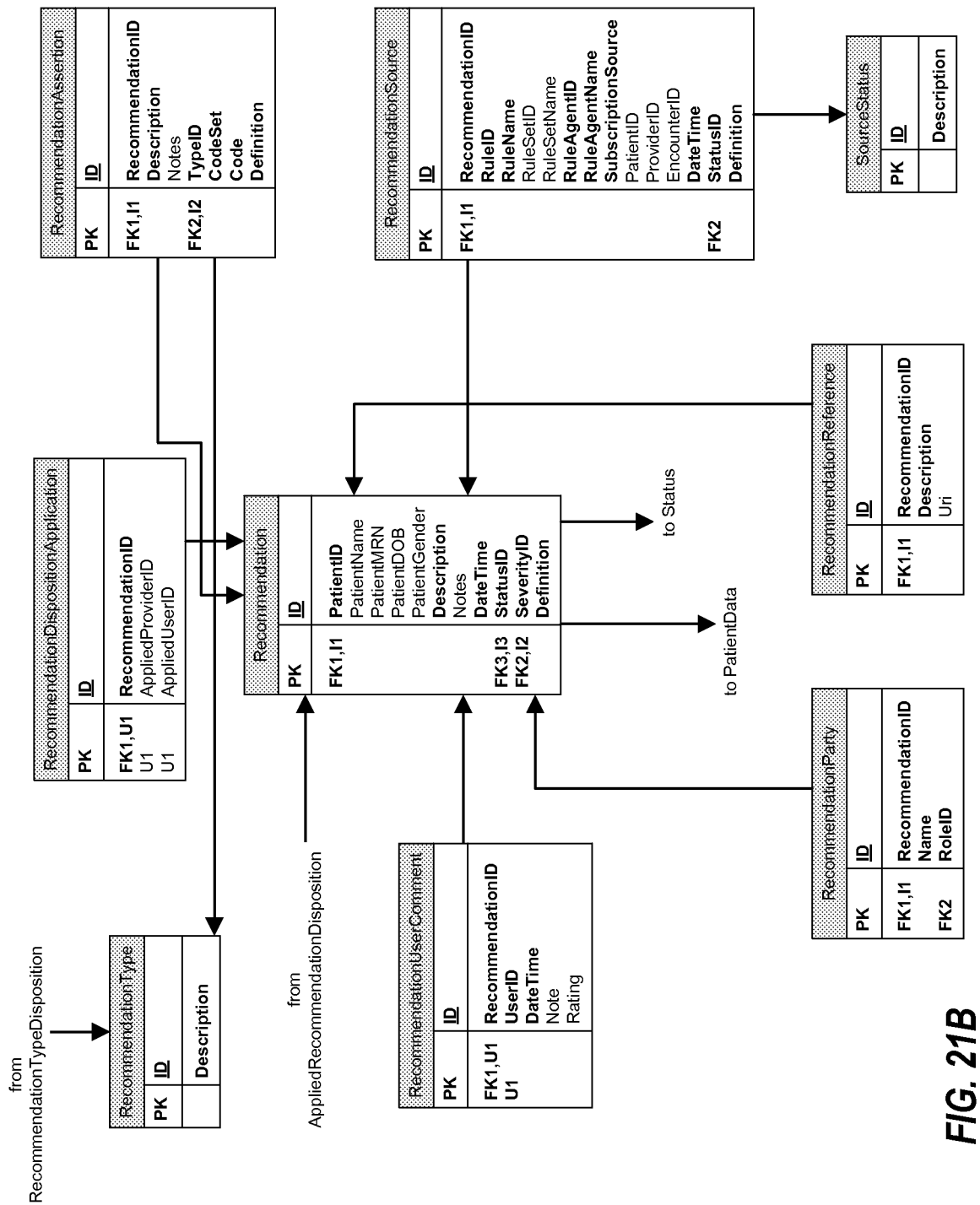

As described herein, the CDS Manager is configured to manage rule definitions and rule subscriptions for providers and organizations. FIGS. 20A and 20B, taken jointly, are a block diagram of a data model for the manager structures of an exemplary clinical decision support system.

Figure 22:
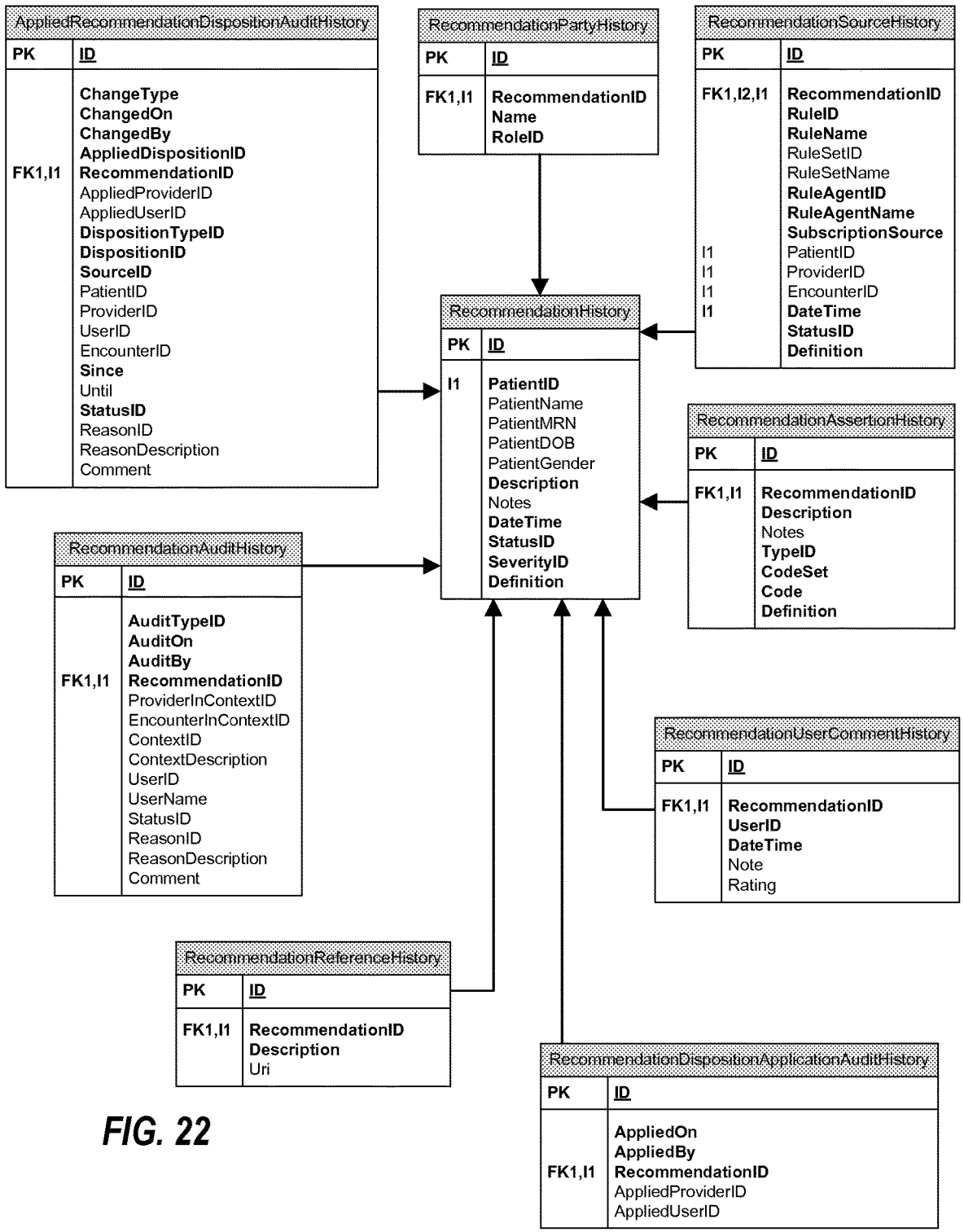
FIG. 22 is a block diagram of a data model for the aggregator history structures of a clinical decision support system in accordance with one or more preferred embodiments of the present invention.

Similarly, FIGS. 21A-23 represent data models for structures associated with aggregation functionality of a CDS System. Specifically, FIGS. 21A and 21B, taken jointly, are a block diagram of a data model for the aggregator structures of a clinical decision support system; FIG. 22 is a block diagram of a data model for the aggregator history structures of a clinical decision support system; and FIG. 23 is a block diagram of a data model for the aggregator audit structures of a clinical decision support system.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

Moreover, although aspects and features of innovative systems, methods, and apparatus described herein are largely described in a medical context, it will be appreciated that such aspects and features are applicable in other contexts as well.

What is claimed is:

1. A method for facilitating the real-time provision of recommendations to a health care provider, comprising the steps of:
receiving, in a processor-based clinical decision support (CDS) system, a user's identity from an electronic health records application and a call to evaluate rules associated with the provision of data relating to health care information;
electronically performing an evaluation of the rules via a CDS rule engine, wherein rule content, patient data, and rule evaluation parameters are provided to the engine, and the engine returns recommendation data triggered by the evaluation;
automatically determining in the CDS system a list of rules subscribed to by a healthcare provider and generating a rule evaluation call including the list of rules and the determined specific healthcare information;
automatically determining specific information necessary to evaluate the rules from the list of rules, such that the determined specific information is a minimum possible set of information necessary to evaluate the subscribed rules during a workflow process;
evaluating, via the CDS rule engine, the electronically communicated rules from the list of rules utilizing the electronically communicated specific healthcare information to produce one or more results based on the evaluation of the rules, the one or more results comprising recommendation data; and
generating the recommendation data comprising message data including only a minimum required information in a request for rule evaluation.

2. The method of claim 1, further comprising receiving, via the electronic health records application, a disposition to apply to the generated recommendation data.

3. The method of claim 1, further comprising modifying one or more subscriptions to one or more rules via an interface of a console.

4. The method of claim 3, wherein said step of modifying one or more subscriptions comprises subscribing to a rule.

5. The method of claim 3, wherein said step of modifying one or more subscriptions comprises unsubscribing to a rule.

6. The method of claim 3, wherein said step of modifying one or more subscriptions comprises subscribing to a particular version of a rule.

7. The method of claim 3, wherein said step of modifying one or more subscriptions comprises indicating a desire for a subscription to automatically be updated to the most current version of a rule.

8. The method of claim 3, wherein determining a list of rules subscribed to by a healthcare provider comprises accessing a cached list of rules subscribed to by a healthcare provider.

9. The method of claim 8, further comprising receiving update information regarding a list of rules subscribed to by a healthcare provider, and updating the cached list of rules.

10. The method of claim 1, wherein the one or more results include one or more suggestions.

11. The method of claim 10, wherein each of the one or more suggestions is associated with a recommendation.

12. The method of claim 10, wherein the one or more suggestions comprise one of a missing data suggestion and/or an out-of-range suggestion.

13. The method of claim 1, wherein at least some of the rule content is parameterized in that rule content corresponding to one or more specific rules contains parameters associated with default or user specified values.

14. One or more non-transitory computer readable media containing computer executable instructions for facilitating the real-time provision of recommendations to a health care provider, comprising:
receiving, in a processor-based clinical decision support (CDS) system, a user's identity from an electronic health records application and a call to evaluate rules associated with the provision of data relating to health care information;
electronically performing an evaluation of the rules via a CDS rule engine, wherein rule content, patient data, and rule evaluation parameters are provided to the engine, and the engine returns recommendation data triggered by the evaluation;
automatically determining in the CDS system a list of rules subscribed to by a healthcare provider and generating a rule evaluation call including the list of rules and the determined specific healthcare information;
automatically determining specific information necessary to evaluate the rules from the list of rules, such that the determined specific information is a minimum possible set of information necessary to evaluate the subscribed rules during a workflow process;
evaluating, via the CDS rule engine, the electronically communicated rules from the list of rules utilizing the electronically communicated specific healthcare information to produce one or more results based on the evaluation of the rules, the one or more results comprising recommendation data; and
generating recommendation data comprising message data including only a minimum required information in a request for rule evaluation.

15. The one or more non-transitory computer readable media of claim 14, further comprising receiving, via the electronic health records application, a disposition to apply to the generated recommendation data.

16. The one or more non-transitory computer readable media of claim 14, further comprising modifying one or more subscriptions to one or more rules via an interface of a console.

17. The one or more non-transitory computer readable media of claim 16, wherein said step of modifying one or more subscriptions comprises at least one of (i) subscribing to a rule, (ii) unsubscribing to a rule, (iii) subscribing to a particular version of a rule, and (iv) indicating a desire for a subscription to automatically be updated to the most current version of a rule.

18. The one or more non-transitory computer readable media of claim 14, wherein the one or more results include one or more suggestions, wherein each of the one or more suggestions (i) is associated with a recommendation, or (ii) comprise one of a missing data suggestion and/or an out-of-range suggestion.

19. The one or more non-transitory computer readable media of claim 18, wherein determining a list of rules subscribed to comprises accessing a cached list of rules subscribed to by a healthcare provider.

20. A method for facilitating the real-time provision of recommendations to a health care provider, comprising the steps of:
- receiving, in a processor-based clinical decision support (CDS) system, a user's identity from an electronic health records application and a call to evaluate rules associated with the provision of data relating to health care information;
- electronically performing an evaluation of the rules via a CDS rule engine, wherein rule content, patient data, and rule evaluation parameters are provided to the engine, and the engine returns recommendation data triggered by the evaluation, wherein at least some of the rule content is parameterized in that rule content corresponding to one or more specific rules contains parameters associated with default or user specified values;
- automatically determining in the CDS system a list of rules subscribed to by a healthcare provider and generating a rule evaluation call including the list of rules and the determined specific healthcare information;
- automatically determining specific information necessary to evaluate the rules from the list of rules, such that the determined specific information is a minimum possible set of information necessary to evaluate the subscribed rules;
- evaluating, via the CDS rule engine, the electronically communicated rules from the list of rules utilizing the electronically communicated specific healthcare information to produce one or more results based on the evaluation of the rules, the one or more results comprising recommendation data; and
- generating recommendation data comprising message data including only a minimum required information in a request for rule evaluation.

* * * * *